(12) United States Patent
Takahashi et al.

(10) Patent No.: US 8,696,603 B2
(45) Date of Patent: Apr. 15, 2014

(54) SYSTEM FOR MEASURING SPACE WIDTH OF JOINT, METHOD FOR MEASURING SPACE WIDTH OF JOINT AND RECORDING MEDIUM

(75) Inventors: Tomoyuki Takahashi, Kanagawa-ken (JP); Noriaki Ida, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 371 days.

(21) Appl. No.: 12/591,875

(22) Filed: Dec. 3, 2009

(65) Prior Publication Data
US 2010/0145231 A1 Jun. 10, 2010

(30) Foreign Application Priority Data

| Dec. 4, 2008 | (JP) | ................................ 2008-310122 |
| Dec. 4, 2008 | (JP) | ................................ 2008-310128 |
| Mar. 31, 2009 | (JP) | ................................ 2009-087492 |
| Mar. 31, 2009 | (JP) | ................................ 2009-087844 |

(51) Int. Cl.
*A61B 5/00* (2006.01)

(52) U.S. Cl.
USPC ........................................................ 600/595

(58) Field of Classification Search
USPC .................................................. 600/587, 595
See application file for complete search history.

(56) References Cited

U.S. PATENT DOCUMENTS

| 7,054,476 B2 | 5/2006 | Oosawa et al. |
| RE43,282 E * | 3/2012 | Alexander et al. ............. 600/427 |
| 8,277,461 B2 * | 10/2012 | Pacheco ........................ 606/102 |
| 2002/0087274 A1 | 7/2002 | Alexander et al. |
| 2002/0177770 A1 | 11/2002 | Lang et al. |
| 2004/0059215 A1 | 3/2004 | Nishimura et al. |
| 2005/0256389 A1 | 11/2005 | Koga et al. |

FOREIGN PATENT DOCUMENTS

| JP | 09-018685 | 1/1997 |
| JP | 09-056706 | 3/1997 |
| JP | 2002-203248 | 7/2002 |
| JP | 2002-532126 A | 10/2002 |
| JP | 2002-541950 A | 12/2002 |
| JP | 2003-126045 A | 5/2003 |
| JP | 2003-144454 A | 5/2003 |
| JP | 2004-275361 | 10/2004 |
| JP | 2007-111123 A | 5/2007 |

(Continued)

OTHER PUBLICATIONS

Tetsuya Kubota et al., 3D Shape Reconstruction of Articular Cartilage of Femoral Head from MR Images on Multiple Plane, Feb. 1997, pp. 669-677, vol. J80-D-II.

(Continued)

*Primary Examiner* — Max Hindenburg
(74) *Attorney, Agent, or Firm* — Jean C. Edwards, Esq.; Edwards Neils PLLC

(57) ABSTRACT

A method for measuring space width of joint includes: a joint image input step of inputting an image of a joint; a contour detecting step of detecting contours of a pair of bones constituting the joint; a measurement range setting step of setting a measurement range of a space of the joint based on the contours detected in the contour detecting step; a space width calculating step of calculating a space width which is a distance between the pair of bones within the measurement range set in the measurement range setting step; and a display step of displaying the space width calculated in the space width calculating step.

32 Claims, 35 Drawing Sheets

(56) References Cited

FOREIGN PATENT DOCUMENTS

| JP | 2007-151742 | 6/2007 |
| JP | 2008-093229 | 4/2008 |
| JP | 2008-173236 A | 7/2008 |
| WO | WO 00/63844 A1 | 10/2000 |

OTHER PUBLICATIONS

Notification of Reasons for Rejection issued by JPO Jul. 4, 2013 in connection with Japanese Patent Application No. 2009-276568, which corresponds to the present application.

* cited by examiner

POSITION ON CONTOUR OF PELVIS ACETABULUM

POSITION ON CONTOUR OF PELVIS ACETABULUM

FIG.20A

```
MEASUREMENT RESULT OF JOINT SPACE

MINIMUM SPACE WIDTH : 1.5mm

AVERAGE SPACE WIDTH : 2.5mm
```

FIG.20B

```
MEASUREMENT RESULT OF JOINT SPACE
<"A" REGION>
MINIMUM SPACE WIDTH : 1.5mm
AVERAGE SPACE WIDTH : 2.5mm
<"B" REGION>
MINIMUM SPACE WIDTH : 2.0mm
AVERAGE SPACE WIDTH : 2.5mm
<"C" REGION>
           ⋮
```

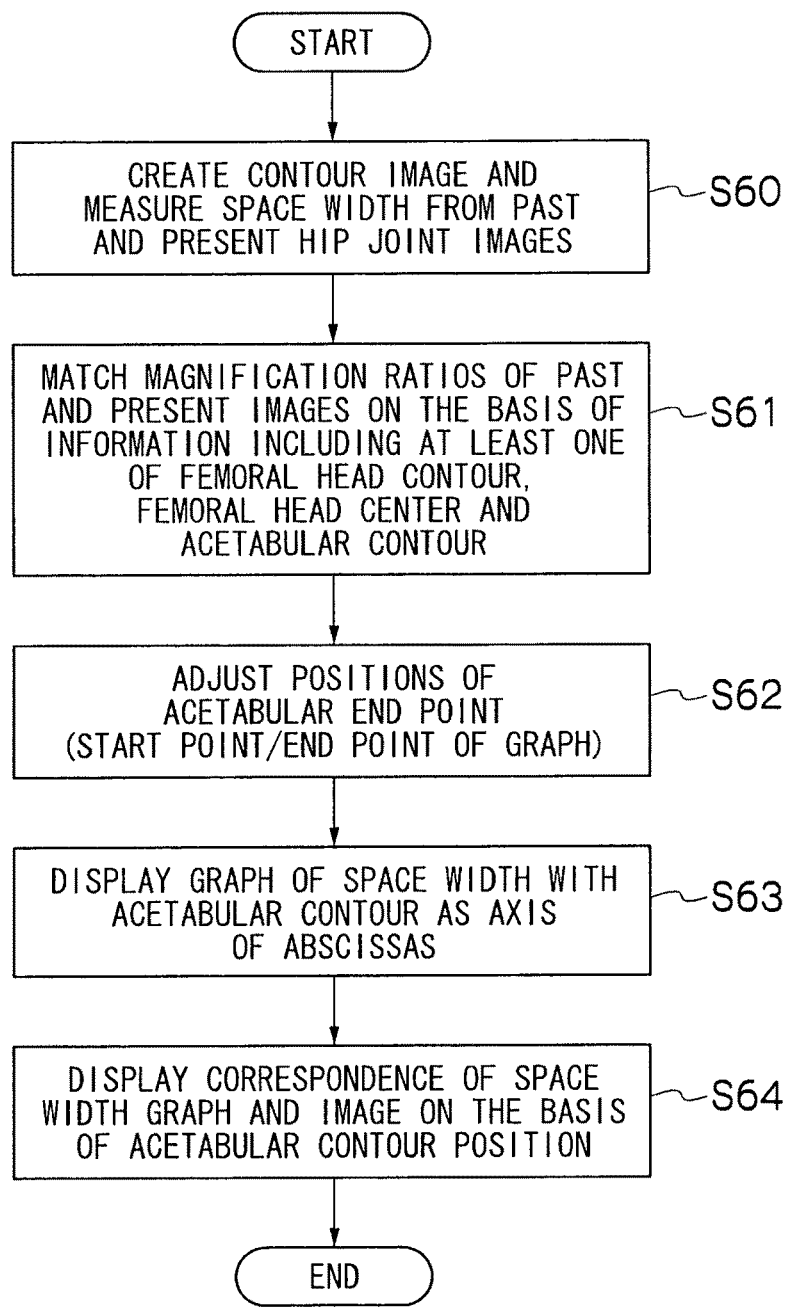

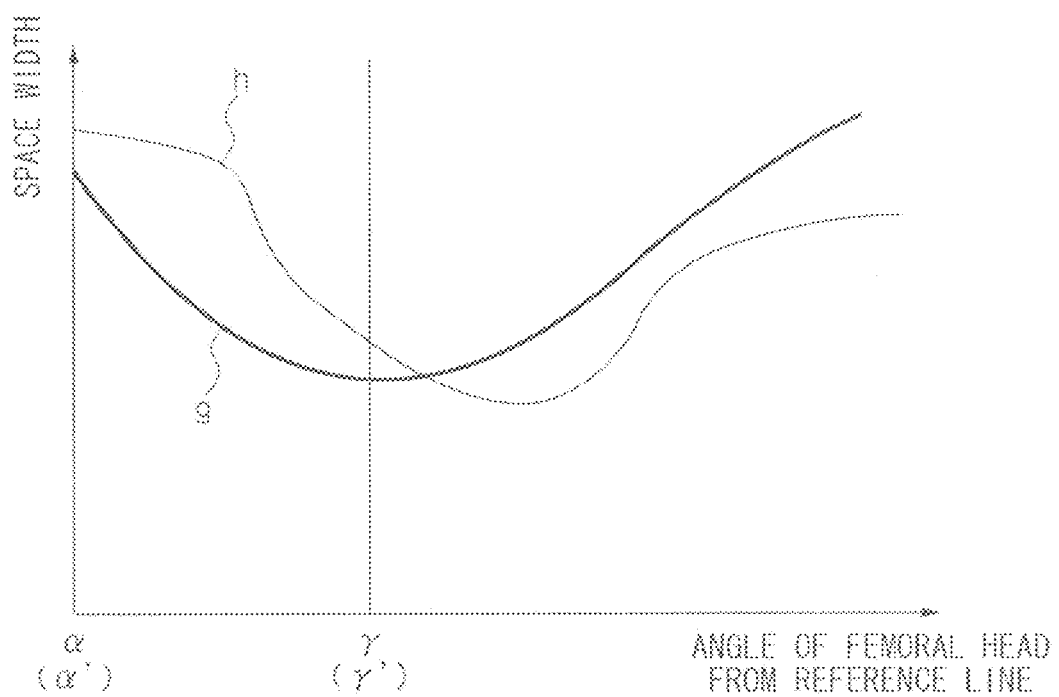

SYSTEM FOR MEASURING SPACE WIDTH OF JOINT, METHOD FOR MEASURING SPACE WIDTH OF JOINT AND RECORDING MEDIUM

CROSS-REFERENCE TO RELATED APPLICATIONS

This application claims the priority benefit under 35 U.S.C. §119 of Japanese Patent Application No. 2008-310122 filed on Dec. 4, 2008, Japanese Patent Application No. 2008-310128 filed on Dec. 4, 2008, Japanese Patent Application No. 2009-87492 filed on Mar. 31, 2009 and Japanese Patent Application No. 2009-87844 filed on Mar. 31, 2009, which are hereby incorporated in its entirety by reference.

BACKGROUND OF THE INVENTION

1. Field of the Invention

The presently disclosed subject matter relates to a system for measuring space width of joint, a method for measuring space width of joint and a recording medium, and particularly relates to the technique of aiding measurement in orthopedic surgery by detecting an anatomical feature point of a human body structure such as a center of a thigh femoral head, and measuring a space width of a joint of a hip joint and comparing images photographed at different times to make the images available for diagnosis of the temporal change of a disease in the hip joint and to perform quantification of evaluation of a space of the joint.

2. Description of the Related Art

Conventionally, diagnosis of a disease such as arthrosis deformans in a hip joint, a knee joint or the like has been performed mainly by X-ray images. In order to make the diagnosis or judgment by a doctor more accurate, it is necessary to provide objective diagnosis information of the position and the like of an anatomical feature point such as a center of a thigh femoral head (a thigh femoral head center), for example.

There is known the system which displays an image obtained by imaging a diagnosis object such as a pelvis, for example, on a display unit, receives information for drawing objects such as a reference line and a parallel line thereof for measuring bending of a body, for example, onto the image from an input unit, draws the objects on the image displayed on the display unit, calculates the value showing the geometric relationship between the drawn objects, and makes the value available for diagnosis of the doctor. The input information which is inputted from the input unit is a point on the image which is manually inputted by a user (doctor or the like), and the objects are drawn by directly using a positional information of the point which is inputted by the user (see, for example, Japanese Patent Application Laid-Open No. 2007-151742).

Further, in the diagnosis of a disease in a hip joint, comparison of a temporal changes of the minimum space width is very useful for diagnosis. There have been conventionally proposed various techniques of comparing images acquired over time, arranging a plurality of images, composing a plurality of images to form one image with high resolution, or displaying images by superimposing them on each other so that the shape of a subject is easily understood.

For example, there is known an image display device which obtains, from a distance calculated from a specific end point of at least any one of a diagnosis image and a reference image, a magnification (or reduction) ratio of the one image, and performs magnification or reduction processing of at least any one of the images so that the diagnosis image and the reference image have substantially the same size based on the ratio to reproduce and display both the images side by side at the same time (see, for example, Japanese Patent Application Laid-Open No. 9-56706).

Further, there is known an image composite method (see, for example, Japanese Patent Application Laid-Open No. 9-18685) in which distortion of each of images sequentially inputted is corrected, a region having a predetermined edge is extracted for each of adjacent images, a plurality of images are bonded to one another, and one high-resolution image is generated. Also, there is known an image display device (see, for example, Japanese Patent Application Laid-Open No. 2004-275361) which generates line images in which geometric characteristics of a subject are represented by line drawing for each of medical images, and displays the line images for a plurality of medical images by superimposing them on each other, thereby making it easy to compare the geometrical characteristics of the subject in the medical image which is a diagnosis object.

Furthermore, there is also known a measurement processor including a measurement point setting device which automatically sets a measurement point for geometrically measuring a measurement object image based on the positional information of the measurement points which are set with respect to the measurement object images photographed at different time points which are obtained by photographing substantially the same region of the same subject in time sequence, and the measurement reference images corresponding to them, and a geometrical information measuring device which geometrically measures the measurement object image based on the positional information of the measurement points set with respect to the measurement object images, so as to keep an eye on developments of the state of the disease of a patient (see, for example, Japanese Patent Application Laid-Open No. 2002-203248).

Further, conventionally, quantification of evaluation of a space of a joint has been performed in order to provide doctors with objective diagnosis information so that the doctors can perform more accurate diagnosis or judgment, and there is known a technique of obtaining upper side and lower side of a region where a cartilage of a knee exists from X-ray image data, and the range in the lateral direction where the cartilage of the knee exists from the X-ray image data, regarding the region surrounding by the upper side and the lower side obtained in the above description in the range in the lateral direction as a region where the cartilage exists, and acquiring a size (square measure) of the region where the cartilage exists (see, for example, Japanese Patent Application Laid-Open No. 2008-93229). Namely, in this case, the size of the region where the cartilage exists corresponds to the size of the space of the joint, and therefore, the space narrowing extent based on the size of the region where the cartilage exists, which is thus acquired, is quantified.

SUMMARY OF THE INVENTION

However, a CE angle (Center Edge Angle), which is one of the evaluation values used in diagnosis of a hip joint region is calculated based on the positional information of a thigh femoral head center, an outer end of a hip cup, and lower ends of left and right tear drop and the like. The thigh femoral head center is defined as the center of a certain structure. Therefore, no mark for showing its position exists on the image. Thus, when a user manually inputs the above described positional information as described in the above described Japanese Patent Application Laid-Open No. 2007-151742, the position of the thigh femoral head center or the like varies each time, depending on the user who inputs the information, the timing of measurement and the like, and accurate diagnosis cannot be performed.

Further, in the diagnosis of a hip joint disease, for example, the measurement position of the minimum space width may differ at present and in the past depending on the advance extent of the disease and treatment, and therefore, there is the problem of being unable to perform accurate diagnosis only by simply comparing the minimum value of the space width numerically.

Thus, when the temporal change of the minimum width is observed in the diagnosis of a hip joint disease, it is desirable to be able to confirm how the space width of the place where the minimum space width was measured in the previous diagnosis has changed in the present diagnosis, and contrary to this, it is desired to confirm the previous position of the place where the minimum space width has been measured this time and the space width thereof. Further, in addition to the minimum space width, there has been such a demand that when a doctor is interested in a space width on one of the present and the past images, the doctor wants to know what the space width is like on the other image. However, due to advanced diseases and the other causes, it has been conventionally very difficult to compare the positions and spaces of the space widths quantitatively between the present and the past images.

The techniques described in the prior art documents such as Japanese Patent Application Laid-Open No. 9-56706, Japanese Patent Application Laid-Open No. 9-18685, Japanese Patent Application Laid-Open No. 2004-275361 and Japanese Patent Application Laid-Open No. 2002-203248 are useful techniques when sequential comparison is performed in image diagnosis, but are unable to perform comparison of the joint space widths as described above or display of the related portions. Further, in the above described prior art documents, when the serial data of the measured space width are displayed by being compared between the past and present, and a plurality of images of the past, present and the like are displayed, the positions and the values of the space widths are not displayed by bringing the related places into correspondence with each other on the respective images, and the line images are only displayed by being superimposed on medical images, thereby causing the problem that advance extent of the disease cannot be diagnosed, and useful diagnosis of a hip joint disease cannot be performed.

Further, in quantification of the joint space evaluation, a joint space generally refers to a space between the bones constituting a joint. When the evaluation value of the joint space is defined by the area of the space between the bones, if a thigh femoral head is displaced with respect to the pelvis acetabulum at the time of evaluating the joint space of the thigh femoral head and the pelvis acetabulum in a hip joint region, for example, the space may increase as an area though space narrowing (the phenomenon in which the cartilage is worn and the space of a joint is narrowed) has advanced. More specifically, there is the problem of existence of the case in which the advance extent of space narrowing and the evaluation value of the joint space cannot be correlated.

Further, as the evaluation value of a joint space, the evaluation index is also generally known, which is the space width that is the distance between the bones constituting the joint, in addition to the area of the space between the bones constituting the joint. However, the definition of how it is calculated on the digital image is not clearly disclosed.

The presently disclosed subject matter is made in view of such circumstances, and has an object to provide a joint space width measuring system, a method for measuring space width of joint and a program which can correlate advance extent of space narrowing and an evaluation value of a joint space.

Further, it is an object of the presently disclosed subject matter to provide a joint space width measuring system, a method for measuring space width of joint and a program which bring related places into correspondence with each other in a plurality of images and display the images with a space width and the like, and can perform useful diagnosis of a hip joint disease including the advance extent of the disease.

In order to attain the above described objects, the first aspect of the presently disclosed subject matter provides a system for measuring space width of joint including: a joint image input unit which inputs an image of a joint; a contour detection unit which detects contours of a pair of bones constituting the joint; a measurement range setting unit which sets a measurement range of a space of the joint based on the contours detected by the contour detection unit; a space width calculation unit which calculates a space width which is indicated by a distance value between the pair of bones in the measurement range set by the measurement range setting unit as a distance value between two points at which a predetermined straight line intersects with the contours of the pair of bones in the measurement range; and a display unit which displays the space width calculated by the space width calculation unit.

Thereby, the space width which is a distance between a pair of bones is calculated based on the detected contour and is displayed, and therefore, the advance extent of joint space narrowing and the evaluation value of the joint space can be correlated.

Further, the second aspect of the presently disclosed subject matter is the system according to the first aspect, further including an information input unit which inputs information to the system, wherein the contour detection unit detects the contours by interpolating a plurality of points on the contour which are inputted by the information input unit.

Thereby, the contour is detected by interpolating a plurality of points on the contour which are inputted by the information input unit. Therefore, the burden on the user is reduced, and an accurate contour can be detected.

Further, the third aspect of the presently disclosed subject matter is the system according to the first aspect, wherein the contour detection unit detects the contours based on a plurality of edge points in an edge image formed by performing edge detection for the image of the joint inputted by the joint image input unit.

Thereby, the contour is detected based on a plurality of edge points in the edge image of the joint, and therefore, a more accurate contour can be detected.

Further, the fourth aspect of the presently disclosed subject matter is the system according to the third aspect, further including an information input unit which inputs information to the system, wherein the plurality of edge points are inputted by the information input unit.

Thereby, a user can detect the contour based on a plurality of edge points inputted in the edge image of the joint.

Further, the fifth aspect of the presently disclosed subject matter is the system according to any one of the first to the fourth aspect, wherein the measurement range setting unit sets a whole of the contours detected by the contour detection unit as the measurement range.

Thereby, the whole of the contours is set as the measurement range, and the space width can be recognized over the whole of the contours.

Further, the sixth aspect of the presently disclosed subject matter is the system according to the first aspect, wherein the predetermined straight line extends radially from a predetermined point.

Further, the seventh aspect of the presently disclosed subject matter is the system according to the sixth aspect, wherein the predetermined point is a femoral head center point.

Further, the eighth aspect of the presently disclosed subject matter is the system according to the first aspect, wherein the predetermined straight line is perpendicular to one fixed straight line different from the predetermined straight line.

Further, the ninth aspect of the presently disclosed subject matter is the system according to the eighth aspect, wherein the fixed straight line is a straight line connecting lower ends of a left and a right tear drops.

Further, the tenth aspect of the presently disclosed subject matter is the system according to any one of the first to the ninth aspect, wherein the space width calculation unit calculates a neighborhood average space width which is an average value of an arbitrary space width of the serial data of a plurality of space widths and one or more neighborhood space widths which are present in a vicinity of the arbitrary space width.

Further, the eleventh aspect of the presently disclosed subject matter is the system according to any one of the first to the ninth aspect, wherein the space width calculation unit calculates a median value of an arbitrary space width of serial data of a plurality of space widths and two or more neighborhood space widths which are present in a vicinity of the arbitrary space width.

Further, the twelfth aspect of the presently disclosed subject matter is the system according to any one of the first to the eleventh aspect, wherein: the space width is a minimum value of serial data of a plurality of space widths, and the display unit displays a portion corresponding to the space width at which the minimum value is calculated by emphasizing the portion.

Further, the thirteenth aspect of the presently disclosed subject matter is the system according to any one of the first to the twelfth aspect, wherein the display unit displays a graph of serial data of a plurality of space widths.

Further, the fourteenth aspect of the presently disclosed subject matter is the system according to the thirteenth aspect, wherein the display unit causes the displayed graph to vary in accordance with a value of the space width.

Further, the fifteenth aspect of the presently disclosed subject matter is the system according to the thirteenth or the fourteenth aspect, wherein: the display unit displays the image of the joint inputted by the joint image input unit, and when an arbitrary point on the displayed graph is designated, a corresponding portion of the contour in the image of the joint is displayed by being emphasized.

Further, the sixteenth aspect of the presently disclosed subject matter is the system according to any one of the first to the fifteenth aspect, wherein the display unit switches a kind of display of the value of the space width in accordance with the value of the space width.

Further, the seventeenth aspect of the presently disclosed subject matter is the system according to any one of the first to the sixteenth aspect, wherein the display unit displays the image of a joint which is inputted from the joint image input unit, and switches a kind of display of the portions corresponding to the contour and the space width in the image of the joint in accordance with a value of the space width.

Further, the eighteenth aspect of the presently disclosed subject matter is the system according to any one of the first to the seventeenth aspect, further including a storage unit which stores at least any one of the image of the joint inputted by the joint image input unit, the space width calculated by the space width calculation unit, and measurement-related information including the contour and the measurement range used for calculating the space width.

Further, the nineteenth aspect of the presently disclosed subject matter is the system according to the eighteenth aspect, wherein the display unit includes an image position adjustment unit which adjusts a position of a present image which is the image of the joint inputted at present by the joint image input unit and a position of a past image which is the image of the joint of the past stored in the storage unit, or adjusts positions of a plurality of the past images to display the images.

Further, the twentieth aspect of the presently disclosed subject matter is the system according to the nineteenth aspect, wherein the display unit includes a display specification adjustment unit which displays the present image and the past image, or the plurality of the past images by superimposing the images on one another, displays the images by switching the images, or displays the images by arranging the images side by side.

Further, the twenty-first aspect of the presently disclosed subject matter is the system according to the nineteenth or the twentieth aspect, wherein the storage unit stores image positioning information including information of positions of the images, orientations of the images and sizes of the images in the display unit when the image position adjustment unit adjusts the positions of the present image and the past image, or the positions of the plurality of the past images.

Further, the twenty-second aspect of the presently disclosed subject matter is the system according to the twenty-first aspect, wherein the image position adjustment unit adjusts the positions of the present image and the past image, or the positions of the plurality of the past images based on the image positioning information stored in the storage unit to display the images.

Further, the twenty-third aspect of the presently disclosed subject matter is the system according to any one of the eighteenth to the twenty-second aspect, wherein the display unit includes an information position adjustment unit which adjusts positions of the measurement-related information of the present and the measurement-related information of the past, or adjusts positions of a plurality of pieces of the measurement-related information of the past to display the information.

Further, the twenty-fourth aspect of the presently disclosed subject matter is the system according to any one of the first to the twenty-third aspect, wherein the joint is a hip joint.

Thereby, useful diagnosis can be performed for a hip joint disease.

Further, the twenty-fifth aspect of the presently disclosed subject matter is the system according to the first aspect, further including: a contour image forming unit which forms a contour image based on contours detected by the contour detection unit; a space width graph creating unit which forms a space width graph in which a position in the joint and a space width are brought into correspondence with each other based on the space width calculated by the space width calculation unit; and a storage unit which stores the image of the joint or the contour image, and the space width graph, wherein: the display unit displays the image of the joint inputted from the image input unit, or the image of the joint stored in the storage unit, or the contour images obtained from these joint images, and the space width graph corresponding to the joint images, and the display unit displays a predetermined point on the image of the joint or the contour image, the predetermined point corresponding to a predetermined point on the space width graph.

Thereby, in diagnosis of a joint, the related places are brought into correspondence with one another in a plurality of images and are displayed with the space width and the like. Then, useful diagnosis of a hip joint disease including the advance extent of the disease can be performed.

Further, the twenty-sixth aspect of the presently disclosed subject matter is the system according to the twenty-fifth aspect, wherein the predetermined point on the space width graph is a point indicating a minimum space width.

Thereby, the user can easily confirm where the position which the minimum space width is measured in the previous measurement time is located this time (present measurement time), or where the position which the minimum space width is measured this time is located at the previous time. The aspect is very useful for comparison in diagnosis.

Further, the twenty-seventh aspect of the presently disclosed subject matter is the system according to the twenty-fifth aspect, further including an information input unit for inputting a designation instruction to designate a predetermined point on the image of the joint, the contour image or the space width graph displayed on the display unit, wherein: a plurality of images of the joint which are inputted at different time points, or a plurality of contour images obtained from the images of the joint are displayed by being arranged side by side on the display unit, a plurality of the space width graphs corresponding to the images of the joint are superimposed on one another, and are displayed on a place different from a place of the display unit on which the image of the joint or the contour image is displayed, and when an arbitrary point on the space width graph is designated, a point on the image of the joint or the contour image, the point corresponding to the arbitrary point is displayed.

Further, as shown in the twenty-eighth aspect of the presently disclosed subject matter is the system according to the twenty-fifth aspect, further including an information input unit for inputting a designation instruction to designate a predetermined point on the image of the joint, the contour image or the space width graph which is displayed on the display unit, wherein: a plurality of images of the joint which are inputted at different time points, or a plurality of contour images obtained from the images of the joint are displayed by being arranged side by side on the display unit, a plurality of the space width graphs corresponding to the images of the joint are superimposed on one another, and are displayed on a place different from a place of the display unit on which the image of the joint or the contour image is displayed, and when a predetermined point on a joint space is designated on the image of the joint or the contour image, a point on the space width graph, the point corresponding to the predetermined point is displayed.

Thereby, the user can easily confirm correspondence of the point on the image of the joint or the contour image, and the point on the space width graph, and can also perform effective diagnosis for the disease of the joint.

Further, as shown in the twenty-ninth aspect of the presently disclosed subject matter is the system according to any one of the twenty-fifth to the twenty-eighth aspect, wherein the space width graph represents an axis of abscissas as a relative position from an acetabular end point of the joint under measurement, and an axis of ordinates as a space width in the relative position of the joint.

Further, as shown in the thirtieth aspect of the presently disclosed subject matter is the system according to any one of the twenty-fifth to the twenty-eighth aspect, wherein the space width graph represents an axis of abscissas as an angle of a half line with a center of a femoral head of the joint under measurement as a start point from a predetermined reference line, and an axis of ordinates as a space width in a position where the half line intersects the space of the joint.

Further, in order to attain the above described objects similarly, the presently disclosed subject matter according to the thirty-first aspect provides a method for measuring space width of joint including: a joint image input step of inputting an image of a joint; a contour detecting step of detecting contours of a pair of bones constituting the joint; a measurement range setting step of setting a measurement range of a space of the joint based on the contours detected in the contour detecting step; a space width calculating step of calculating a space width which is a distance between the pair of bones within the measurement range set in the measurement range setting step; and a display step of displaying the space width calculated in the space width calculating step.

Further, in order to attain the above described objects similarly, the presently disclosed subject matter according to the thirty-second aspect provides a method for measuring space width of joint including: a contour image forming step of forming a contour image by detecting contours of a pair of bones constituting the joint from a plurality of images of a joint, the images being obtained by photographing a joint of a same subject at different time points; a space width calculating step of calculating a space width which is a distance between a pair of bones of the joint in a measurement range set in advance; a space width graph creating step of creating a space width graph in which the calculated space width is brought into correspondence with a position in the space of the joint, for each of the plurality of images of the joint; and a display step of displaying the plurality of joint images or the contour images obtained from the images of the joint by arranging the images side by side on a display screen, displaying a plurality of the space width graphs corresponding to the plurality of images of the joint on a place different from a place where the images of the joint or contour images are displayed by superimposing the graphs, and displaying information which represents a correspondence relation of a predetermined point on the space width graph and a point on the image of the joint or the contour image.

Thereby, in diagnosis of a joint, the related places are brought into correspondence with each other in a plurality of images and are displayed with the space width and the like, and useful diagnosis of a hip joint disease including the advance extent of the disease can be performed.

Further, in order to attain the above described objects similarly, the presently disclosed subject matter according to the thirty-third aspect provides a recording medium including a computer program causing a computer to execute a process for measuring a joint space width, the process including: a joint image input step of inputting an image of a joint; a contour detecting step of detecting contours of a pair of bones constituting the joint; a measurement range setting step of setting a measurement range of a space of the joint based on the contours detected in the contour detecting step; a space width calculating step of calculating a space width which is a distance between the pair of bones within the measurement range set by the measurement range setting step; and a display step of displaying the space width calculated in the space width calculating step.

Thereby, the space width which is the distance between the pair of bones is calculated based on the detected contour and is displayed, and therefore, the advance extent of joint space narrowing and the evaluation value of the joint space can be correlated.

Further, in order to attain the above described objects similarly, the presently disclosed subject matter according to the thirty-fourth aspect provides a recording medium including a computer program causing a computer to execute a process for measuring a joint space width, the process including steps of: detecting contours of a pair of bones constituting a joint from an inputted image of the joint; setting a measurement range of a space width of the joint based on the detected contours; calculating a space width which is a distance between the pair of bones in the set measurement range; forming a contour image based on the detected contours; forming a space width graph in which a position in the joint and the space width are brought into correspondence with each other based on the calculated space width; storing the image of the joint or the contour image, and the space width graph; displaying the inputted image of the joint or the stored image of the joint, or contour images obtained from the images of the joint, and the space width graph corresponding to these joint images on a display screen; and performing processing of displaying a predetermined point on the image of the joint or the contour image, the points corresponding to a predetermined point on the space width graph on the display screen.

Thereby, in diagnosis of a joint, related places are brought into correspondence with one another in a plurality of images and are displayed with the space width and the like, and useful diagnosis of a hip joint disease including the advance extent of the disease can be performed.

As described above, according to the presently disclosed subject matter, the space width that is the distance between a pair of bones is calculated based on the detected contours and is displayed. Therefore, the advance extent of space narrowing and the evaluation value of the joint space can be correlated. Further, in diagnosis of a joint, related places are brought into correspondence with one another in a plurality of images and are displayed with the space width and the like, and useful diagnosis of a hip joint disease including the advance extent of the disease can be performed.

BRIEF DESCRIPTION OF THE DRAWINGS

FIGS. 20A and 20B are explanatory diagrams of a display example 2 of a result of calculation;

FIG. 31 is a flowchart showing a process of a second display method concerning display of a measurement result of a space width of a joint;

FIG. 36 is a chart showing an example of a space width graph in the fourth display method;

DETAILED DESCRIPTION OF THE PREFERRED EMBODIMENTS

Hereinafter, a system for measuring space width of joint, a method for measuring space width of joint and a program according to the presently disclosed subject matter will be described in detail with reference to the attached drawings.

Figure 1:
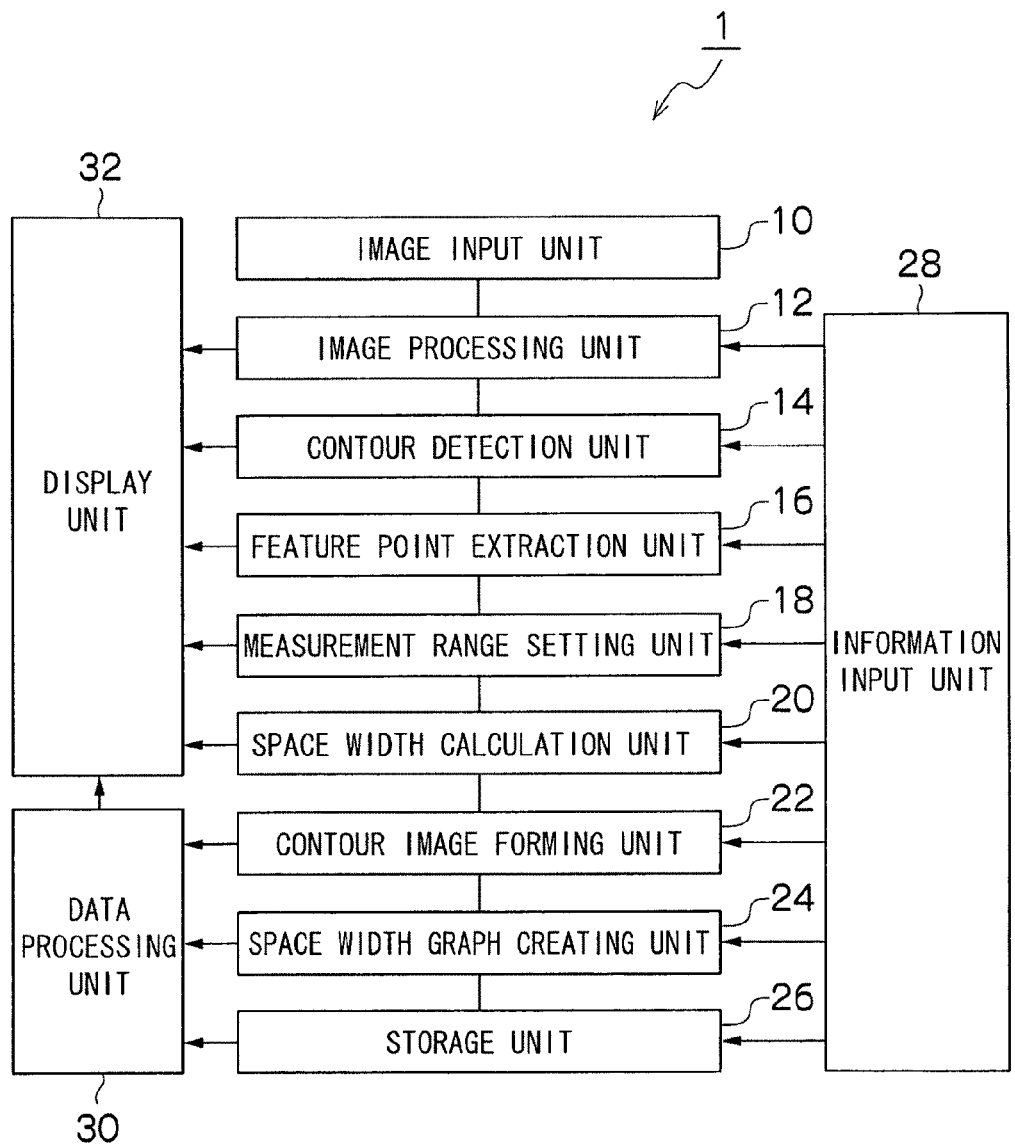
FIG. 1 is a block diagram of a system for measuring space width of joint.

FIG. 1 is a block diagram showing a schematic configuration of one embodiment of the system for measuring space width of joint according to the presently disclosed subject matter.

As shown in FIG. 1, a system 1 for measuring space width of joint of the present embodiment includes an image input unit 10, an image processing unit 12, a contour detection unit 14, a feature point extraction unit 16, a measurement range setting unit 18, a space width calculation unit 20, a contour image forming unit 22, a space width graph creating unit 24, a storage unit 26, an information input unit 28, a data processing unit 30 and a display unit 32.

The image input unit 10 receives X-ray image data obtained by radiographing an examined region of a patient. The method for inputting X-ray image data into the image input unit 10 is not especially limited, and various methods are conceivable.

For example, X-ray image data may be obtained as a radiographic image (CR image) including an image of a bone part (for example, a thigh bone and the like) by using a CR (computed radiographic) system. More specifically, in an radiographing device, the X-ray emitted from an X-ray tube is irradiated to a patient as a subject, and the X-ray which is transmitted through the subject is caused to be incident on an imaging plate having storing phosphors so that the transmitted radiographic image is stored and recorded as energy information, and the transmitted radiographic image may be read from the imaging plate storing and recording the transmitted radiographic image to be inputted in the image input unit 10.

Further, the image input unit 10 may receive the X-ray image data from a digital X-ray photographing device loaded with an FPD (Flat-Panel Detector), the X-ray image data may be inputted from an image server via a network, or the X-ray image data may be inputted from a recording medium such as a CD-ROM.

The image processing unit 12 receives the X-ray image date inputted from the image input unit 10, and performs predetermined image processing for it, and thereafter, delivers the X-ray image date to the display unit 32 and the contour detection unit 14.

The contour detection unit 14 performs detection processing by approximation with a certain curve (closed curve or a part of a closed curve) with respect to the contour of a pair of bones constituting a joint detected from the X-ray image data, for example, the contour (edge) of a human body structure such as a pelvis acetabulum and a thigh femoral head in a hip joint. Though details will be described later, in the case of, for example, a thigh femoral head, an ellipse is the most preferably used as the closed curve for approximating the femoral head contour.

The feature point extraction unit 16 extracts an anatomical feature point of a human body structure. As the feature point extracted here, for example, a femoral head center, an acetabular end point and the like are cited. When the contour of a human body structure is approximated by a closed curve in the contour detection unit 14 above, the anatomical feature point is detected by obtaining the center of gravity of the region enclosed by the closed curve. For example, when femoral head is approximated by an ellipse, the center of the ellipse (the same as the center of gravity in this case) is detected as the femoral head center.

The feature point extraction unit 16 also calculates a CE angle (Center Edge Angle), a Sharp angle, AHI (Ace tabular Head Index) and the like in the case of a hip joint, for example, as predetermined measurement values of a human body structure by using a measurement candidate point which is narrowed down to one. Here, for example, the CE angle is an angle α which is formed by a straight line orthogonal to the straight line connecting a left and right tear drop lower ends M and N, and the straight line connecting an outer end point Q of a hip cup and a center point C of thigh femoral head (a thigh femoral head center point C) in a hip joint front image shown in FIG. 3. Instead of calculating the measurement values of the CE angle, the Sharp angle, AHI and the like at the feature point extraction unit 16, a measurement value calculation unit for measuring them may be additionally provided.

The measurement range setting unit 18 sets the measurement range of a space width, and the space width calculation unit 20 calculates the space width. The space width is a distance (width) between a pair of bones in a joint.

The contour image forming unit 22 creates a contour image formed by only contours such as a femoral head contour and an acetabular contour from the image (joint image) inputted from the image input unit 10.

The space width graph creating unit 24 creates a space width graph expressed by plotting the position of the joint space on the axis of abscissas and plotting the value of the space width in the space position on the axis of ordinates by bringing (the value of) the space width calculated above into correspondence with the position of the joint space.

The storage unit 26 stores the image (joint image) which is inputted from the image input unit 10 and is subjected to predetermined processing, the contour image formed from this, the space width graph and the information related to them in accordance with necessity. When diagnosis is desired to be performed by comparing the image photographed at present and the past image of the same region as the present image, the past image stored in the storage unit 26 is called and displayed.

The information input unit 28 is for a user to input a point which seems to be a point on the contours of a pair of bones constituting a joint into the contour detection unit 14 by seeing the image displayed on the display unit 32, input a point which seems to be an anatomical feature point of a human body structure, and input various instructions to the system. The information input unit 28 includes an operation member for ordinary input such as a keyboard and a mouse, for example, but is not limited to this.

Mainly in the case of displaying a plurality of images, for example, a present diagnosis image and a past diagnosis image on the display unit 32 by superimposing them on each other or arranging them side by side, the data processing unit 30 creates an image for display to be displayed in such a manner. Further, when the diagnosis image (contour image) and the space width graph corresponding to it are displayed, the data processing unit 30 performs processing of bringing a point on the graph into correspondence with a point on the image, and performs various kinds of other processing.

The display unit 32 has a display screen such as an LCD, and displays a medical image such as an X-ray image which is inputted from the image input unit 10 and is subjected to predetermined image processing in the image processing unit 12, the other contour images, a space width graph and the like. At this time, the display unit 32 not only displays each of the images individually, but may display a contour image expressing a contour or the like of a thigh femoral head or the like by superimposing the contour image on the medical image expressing the above described joint. Further, the display unit 32 displays the measurement range set in the measurement range setting unit 18, and displays the measurement value calculated in the space width calculation unit 20.

A user such as a doctor can perform diagnosis by seeing the display screen of the display unit 32. Though not illustrated, the present system 1 for measuring space width of joint preferably includes a printer which prints out an image and the like displayed on the display screen, a storage device which stores various data or a recording device which records these data in various recording media.

Next, as the operation of the system 1 for measuring space width of joint of the present embodiment, the process up to calculation of the space width from the X-ray image obtained by X-ray photographing of a hip joint will be described first. Here, the process will be described with a hip joint taken as an example, but the presently disclosed subject matter is also properly applicable to joints (knee joint, an elbow joint and the like) other than a hip joint.

Figure 2:
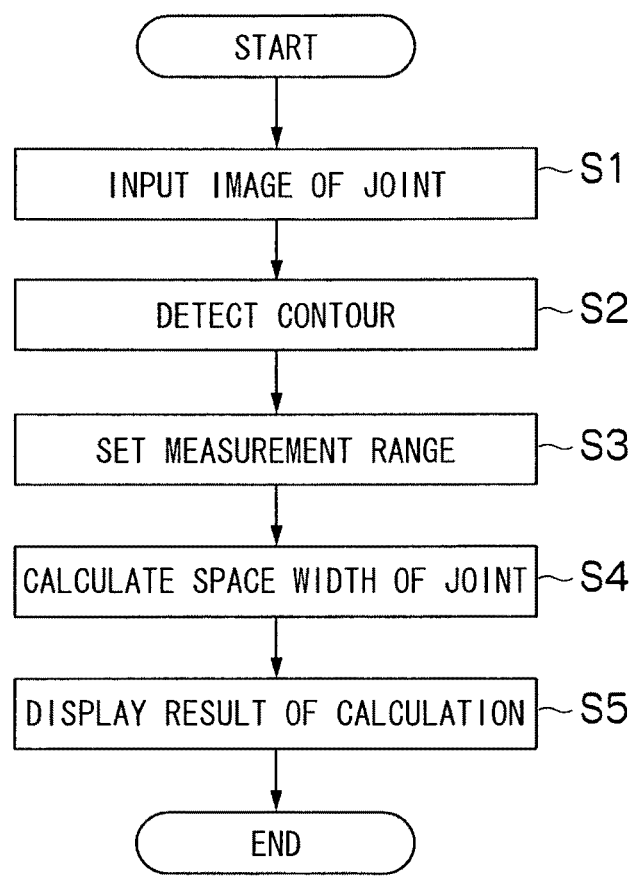
FIG. 2 is an overall flowchart of a process of measuring space width of joint.

FIG. 2 shows a flowchart expressing a flow of a process of a method for measuring space width of joint. As shown in FIG. 2, the process of the method for measuring space width of joint in the present embodiment includes a joint image input step (step S1), a contour detecting step (step S2), a measurement range setting step (step S3), a space width calculating step (step S4) and a calculation result display step (step S5).

First, in step S1 of FIG. 2, the image of a hip joint is inputted from the image input unit 10. As described above, various methods are conceivable as the input method of the image data, and the input method is not especially limited. The image (X-ray image data) of the hip joint of the measurement object which is inputted is sent to the image processing unit 12, is subjected to predetermined image processing, displayed on the display screen of the display unit 32, and is sent to the contour detection unit 14 and the other parts.

Figure 3:
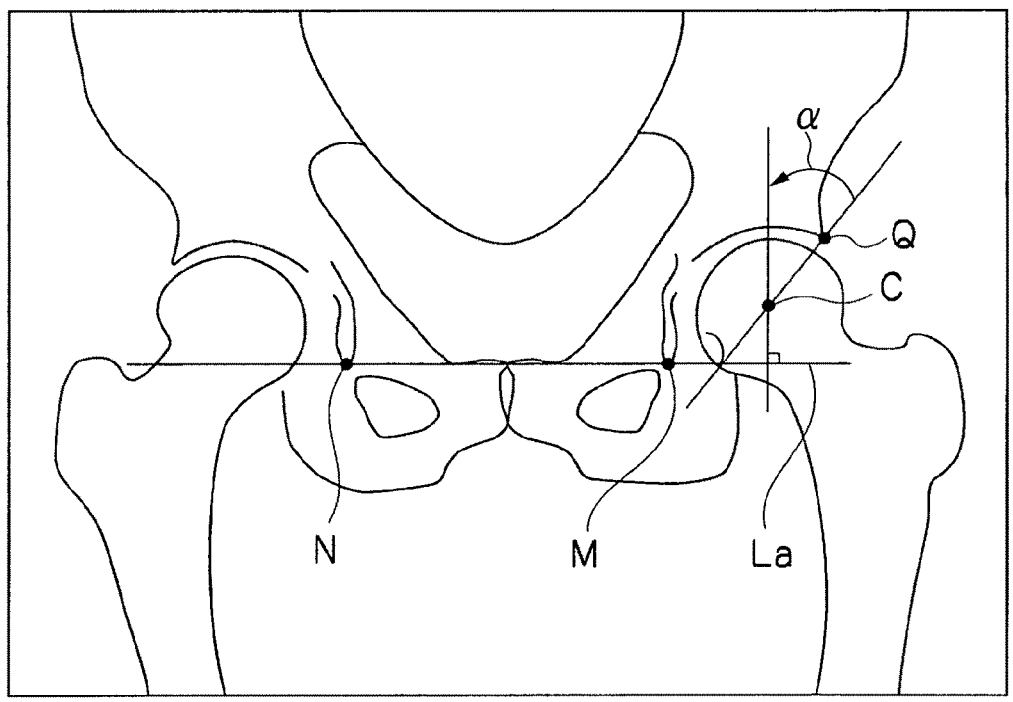
FIG. 3 is an explanatory view showing an example of a front image of a hip joint.

FIG. 3 shows an example of the image of the hip joint displayed on the display screen of the display unit 32. As shown in FIG. 3, the image of the hip joint which is inputted now is a front image of a hip joint on which a thigh femoral head and a pelvis come out (FIG. 3 is expressed as if it were an image in which only the contour shape of each part is drawn, but is actually an X-ray image).

Next, in step S2, the contours of the thigh femoral head and pelvis acetabulum are detected in the contour detection unit 14 which receives the image data after image processing from the image processing unit 12.

As the method for detecting the contours of a thigh femoral head and a pelvis acetabulum, for example, a method for detecting the contours from the information manually inputted by a user in the information input unit 28 is conceivable, but the contours may be detected automatically or semi-automatically in the contour detection unit 14.

Using the input unit 28, the user clicks and inputs a plurality of points on the contours of the thigh femoral head and pelvis acetabulum in the image of the hip joint displayed on the display unit 32 shown in FIG. 3. Thereupon, the contour detection unit 14 recognizes a plurality of points which are clicked, and sets the line connecting the plurality of clicked points by, for example, spline interpolation as a contour line. Thereby, the contours of the thigh femoral head and pelvis acetabulum are detected.

Hereinafter, the method for detecting the thigh femoral head contour will be described in detail.

Figure 4:
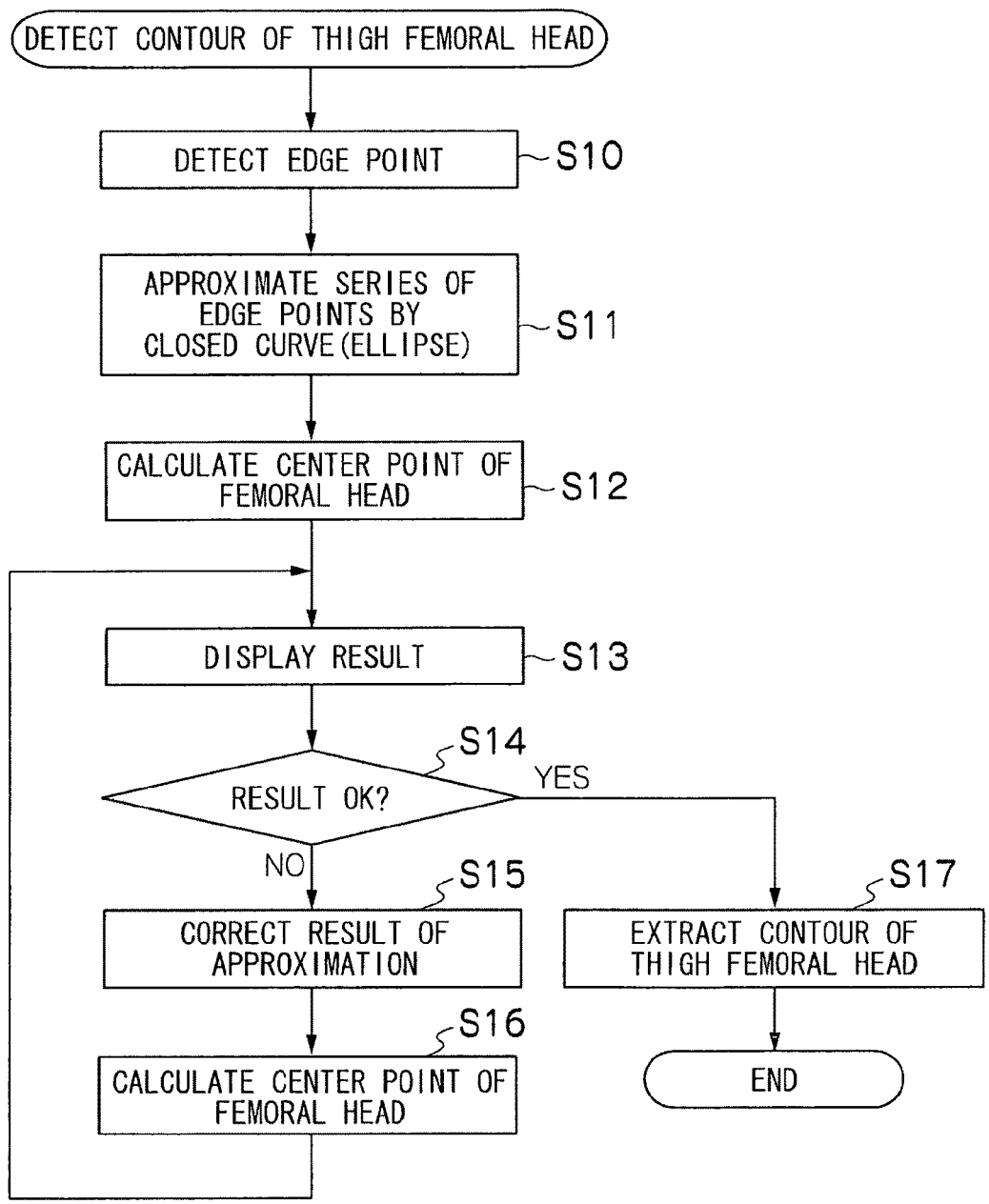
FIG. 4 is a flowchart showing a process of a method for detecting a thigh femoral head contour.

FIG. 4 is a flowchart showing a flow of a process of the method for detecting the thigh femoral head contour.

First, in step S10 of FIG. 4, in the image processing unit 12, the edge of a thigh femoral head is detected by edge detection processing in the ordinary image processing.

Figure 5A:
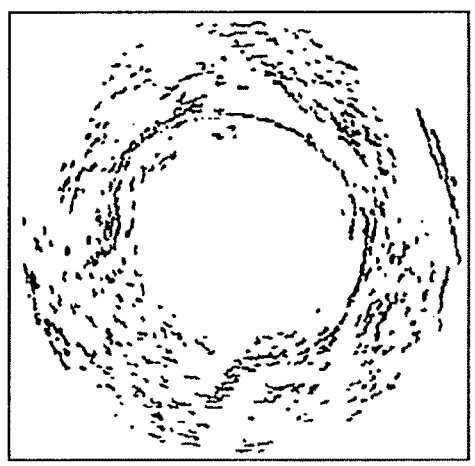
FIG. 5A is an explanatory view showing an image of a cutout local region which includes a thigh femoral head, which is displayed on a display unit.

At this time, as shown in FIG. 5A, for example, the image with the local region where the femoral head comes out being cut out is displayed on the display unit 32. Various methods for creating such a local region image are conceivable, and there are cited the method in which a rough femoral head center position is inputted from the information input unit 28, for example, and the part in its vicinity is cut out, and the like.

Figure 5B:
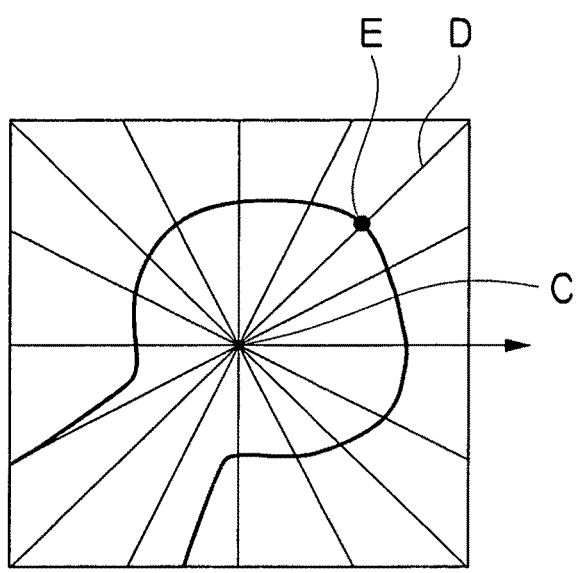
FIG. 5B is an explanatory view showing one example of edge detection.

Further, there are various methods for detecting the edge of the femoral head from the image with the local region of the femoral head being cut out as FIG. 5A, and the method is not especially limited. As one method, for example, as shown in FIG. 5B, a half-line D is radially drawn with an arbitrary point which seems to be substantially the femoral head center point C (see FIG. 3) as the center (start point) (this point is also expressed by C in FIG. 5B), and a point E with a large density change on the half-line D is found, and the point E may be set as the edge. At this time, the substantial center point or the arbitrary point in the femoral head which becomes the start point C of the half-line D is inputted by the user from the information input unit 28.

Alternatively, a method for extracting the edge by applying an ordinary edge extraction filter such as a Sobel filter and a Laplacian filter to the image of FIG. 5A may be adopted.

Next, in step S11 of FIG. 4, the edge which is obtained above is approximated by the closed curve. Here, an ellipse is used as the closed curve for approximating the edge here, but the closed curve is not limited to an ellipse, and may be another curve.

FIG. 6 shows the method for approximating the edge by an ellipse.

Figure 6A:
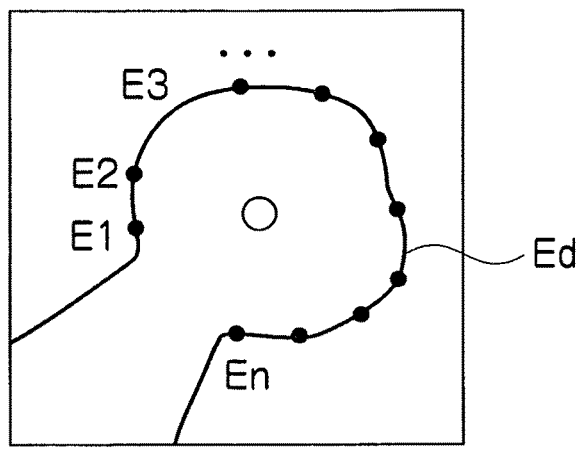
FIGS. 6A to 6C are explanatory views showing a method of approximating an edge by an ellipse.

First, as shown in FIG. 6A, a user designates a plurality of points E1 (x1, y1), E2(x2, y2), E3(x3, y3), . . . , En(xn, yn) on the edge Ed detected above from the information input unit 28.

A user may input these points as edge candidate points from the information input unit 28 by seeing the image displayed on the display unit 32 without detecting the Edge Ed, instead of designating these points on the edge Ed like this.

The expression of the ellipse for approximating the edge Ed (or the ellipse on which the edge candidate points are placed) is given as follows.

$$\{(x-xc)\cos\theta+(y-yc)\sin\theta\}^2/a^2+\{(x-xc)\sin\theta-(y-yc)\cos\theta\}^2/b^2-1=0$$

Figure 6B:
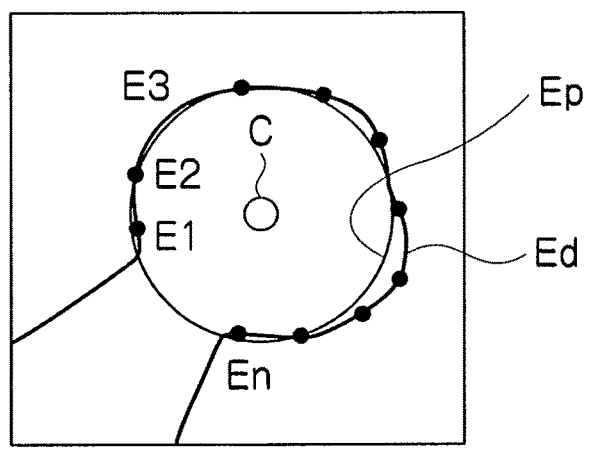
Figure 6C:
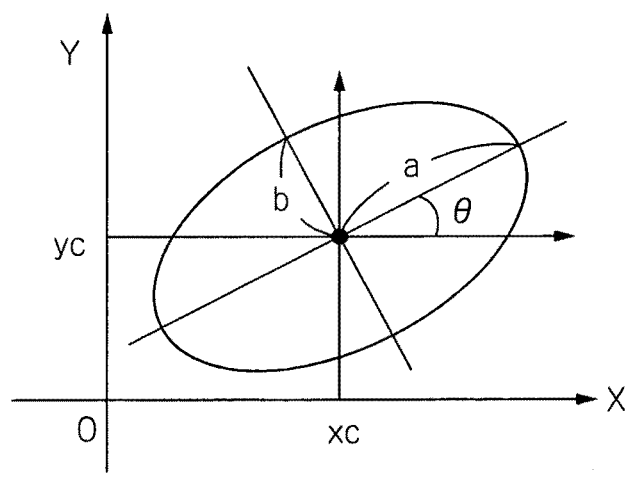

Here, as shown in FIG. 6C, (xc, yc) represents the coordinates of the center of the ellipse, a represents the long axis, b represents the short axis, and θ represents the angle of rotation of the long axis and short axis around the center. In FIG. 6C, for explanation, the ellipse is displayed by being significantly deformed to be easily understood, but the actual approximation ellipse differs from this, and is in a shape significantly close to a circle.

The left side of the above described expression is set as f(xc, yc, θ, a, b, x, y).

With respect to a point Ei(xi, yi) (i=1, . . . , n) on each edge, the following expression is calculated.

$$g(xi,yi)=|f(xc,yc,\theta,a,b,xi,yi)|^{1/2}$$

Here, a symbol |A| represents the absolute value of "A", and $A^{1/2}$ represents the square root of "A".

Here, "Thr" is set as a predetermined threshold value, and the number "N" of points (or edge candidate points) Ei(xi, yi) on the edge which satisfies g(xi, yi)<Thr is calculated.

If the point Ei(xi, yi) is on the ellipse, f(xc, yc, θ, a, b, x, y)=0 is satisfied, and therefore, g(xi, yi)=0. Generally, the value g(xi, yi) expresses the deviation of the point Ei(xi, yi) from the circumference of the ellipse, and as the number "N" of the points at which the deviation becomes smaller than the predetermined threshold value "Thr" is larger, the ellipse f(xc, yc, θ, a, b, x, y)=0 favorably approximates the edge "Ed".

Thus, the number "N" of the points Ei(xi, yi) at which g(xi, yi)<Thr is satisfied, the value obtained by dividing the number "N" by the area of the ellipse, the total of the numbers obtained by multiplying the inverse number of the distance from the approximation ellipse by the respective g(xi, yi) (i=1 to N) and the like are calculated as the evaluation values of approximation.

By changing each of the parameters such as xc, ye, θ, a and b, the parameters which make the above described evaluation value the maximum are sought, whereby, as shown in FIG. 6B, the ellipse "Ep" for approximating the edge "Ed" is detected.

Here, the threshold value Thr is not especially limited, but may be set as 5% to 10% of the long axis or the short axis of the ellipse, for example.

Next, in step S12 of FIG. 4, the femoral head center point is calculated. As shown in FIG. 6B above, the ellipse "Ep" for approximating the edge "Ed" of the femoral head is detected, and therefore, the femoral head center point C is calculated as the center (the same if it is called the center of gravity) of the approximation ellipse "Ep".

Next, in step S13, these detection results are displayed by being superimposed on the image on the display screen of the display unit 32.

Next, in step S14, a user judges whether the approximation ellipse is suitable by seeing the result displayed on the display unit 32.

If there are a number of points Ei(xi, yi) on the edge which are significantly deviated from the approximation ellipse "Ep" which is detected above, correction of the approximation result is performed in the next step S15.

More specifically, the point on the femoral head contour region which should be originally passed is designated on the display screen of the display unit 32 from the information input unit 28. For example, the point may be clicked with a mouse or the like. Subsequently, while the parameters xc, yc, θ, a and b are changed again so that the above described evaluation values becomes higher as the ellipse passes a region nearer to the point, the evaluation reference of the approximation ellipse Ep is changed and calculation is performed again. As a new evaluation value, for example, use of the value obtained by dividing the evaluation value calculated above by the distance of the point designated now and the approximation ellipse, and the like are conceivable. The ellipse by which the evaluation value becomes the maximum is set as a new approximation ellipse.

When the new approximation ellipse Ep is detected, the femoral head center is detected as the center of the approximation ellipse Ep in step S16, the result is displayed again in step S13, and this is performed until a proper approximation ellipse Ep is detected.

When a proper approximation ellipse Ep is detected, the thigh femoral head contour is extracted from the detected approximation ellipse Ep in step S17.

In concrete, the edge points Ei on the circumference of the approximation ellipse and in its vicinity are searched first.

The range in which the edge points Ei are continuously present on the circumference of the approximation ellipse Ep is determined as the portion which can be approximated by the approximation ellipse Ep, and the circumferential shape of the approximation ellipse Ep is extracted as the thigh femoral head contour from the local region image on which the thigh femoral head comes out.

Figure 7:
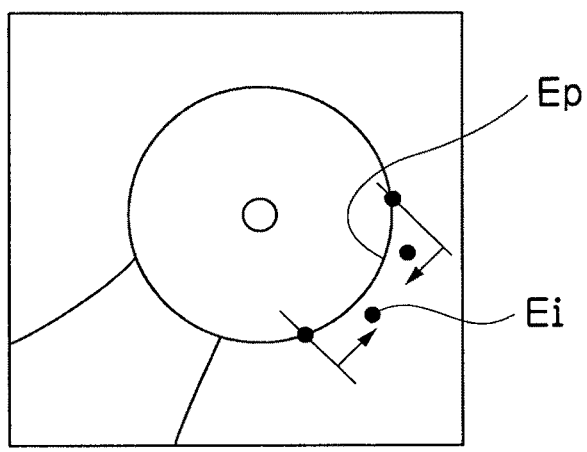
FIG. 7 is an enlarged view showing a thigh femoral head portion.

Meanwhile, the range, which is deviated from the circumference of the approximation ellipse Ep, and in which the edge points "Ei" are continuously present in its vicinity is determined as the portion which cannot be approximated by the approximation ellipse Ep. Thus, as shown by the arrows in FIG. 7, the edge points Ei which are continuously present are connected to one another from both ends of the range which is deviated from the circumference of the approximation ellipse Ep, and in which the edge points Ei are continuously present in its vicinity, toward the center of the range, and the shape which is formed thereby is extracted as the thigh femoral head contour from the local region image on which the thigh femoral head comes out. In order to connect the edge points Ei to one another, a known proper interpolation method can be applied. The operation may be performed automatically, or may be performed semi-automatically by being instructed by a user.

When extraction of the thigh femoral head contour ends in failure, the point on the contour which should be originally passed is clicked, whereby the edge point Ei at the nearest position from the point is set as a relay point of the search range. Subsequently, the region from both ends of the original search range to the relay point is set as a new search range, and the edge points Ei are connected toward the center.

From the above, the thigh femoral head contour is detected.

When the edge is approximated by the ellipse like this, the approximation precision is increased by gradually increasing the resolution from the image with a low resolution.

In the example described above, the point which seems to be a substantial center point or an arbitrary point in the bone center are designated by a user, and thereafter, the half lines are automatically drawn radially from the point to approximate the edge by the ellipse. However, the edge may be approximated by the closed curve other than an ellipse. In this case, the femoral head center is detected as the center of gravity of the closed region enclosed by the closed curve. Alternatively, the operations from edge detection to calculation of the femoral head center by calculating the center by approximation by the ellipse may be performed completely automatically. At this time, approximation of the edge may be performed by the closed curve other than an ellipse, and the center of gravity of the closed region enclosed by the closed curve may be automatically calculated.

Alternatively, a so-called semi-automatic method may be adopted, in which a user manually inputs a plurality of candidate points on the edge and configures the approximation form of the edge without approximating the edge automatically by the close curve as above, thereafter, the user automatically obtains the coordinates of the points on the image, and the femoral head center is detected as the center of gravity of the coordinates.

Figure 8A:
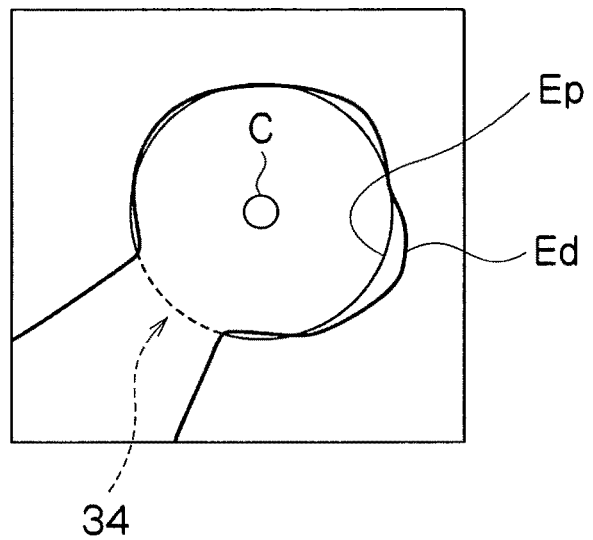
FIGS. 8A and 8B are explanatory views each showing a method for detecting a center when an edge is approximated by using a part of an ellipse.
Figure 8B:
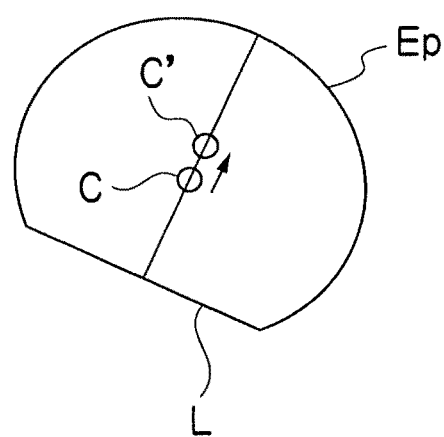

When the edge Ed of the thigh femoral head is not present for the reason of absence of the edge candidate points at the thigh bone side of the femoral head and the like as shown by the broken line 34 in FIG. 8A, the portion of the edge Ed, where the candidate points are absent, is replaced with the straight line L as shown in FIG. 8B, so that the edge Ed of the femoral head includes a part of the ellipse Ep and the straight line L.

The femoral head region is made the region enclosed by a part of the ellipse Ep and the straight line L like this, the center (center of gravity) of this region is considered to be deviated from the center C of the approximation ellipse Ep as obtained above. In this case, a point C' which slightly deviates on the short axis from the center C of the approximation ellipse Ep, for example, is considered to be the femoral head center. This point is calculated as the center of gravity of the region enclosed by a part of the approximation ellipse Ep and the straight line L, for example. Alternatively, the point may be calculated so as to determine the shift amount of the center on the axis of the ellipse from the ratio of the length of the straight line L with respect to a part of the approximation ellipse Ep (cut degree of the ellipse Ep).

Thus, in this case, the shape (edge) of a thigh femoral head as an example of a human body structure is approximated by a closed curve (ellipse) or a part of the closed curve, or the closed region, and the center of gravity of the region (closed region) enclosed by the closed curved is detected as the anatomical feature point of a human body structure. Further, the detection result is displayed by being overlaid on the input image.

According to the above described example, the edge is approximated, and based on this, the center is detected. Therefore, as compared with the case of a user directly inputting the center of a human body structure (thigh femoral head in this case) as in the conventional example, variation of the center point position due to manual input of each user can be suppressed. As a result, reproducibility of the thigh femoral head center point position is enhanced. Therefore, reproducibility of CE angle measurement, for example, is also enhanced, and diagnosis with higher precision is enabled. Further, the approximated shape of a human body structure and the center point thereof are displayed by being overlaid on the input image, whereby success or failure in center point detection can be confirmed. Therefore, by performing correction of the center point detection is performed in accordance with necessity, center point detection precision can be enhanced more.

Next, a method for detecting the contour of the pelvis acetabulum will be described.

Figure 9:
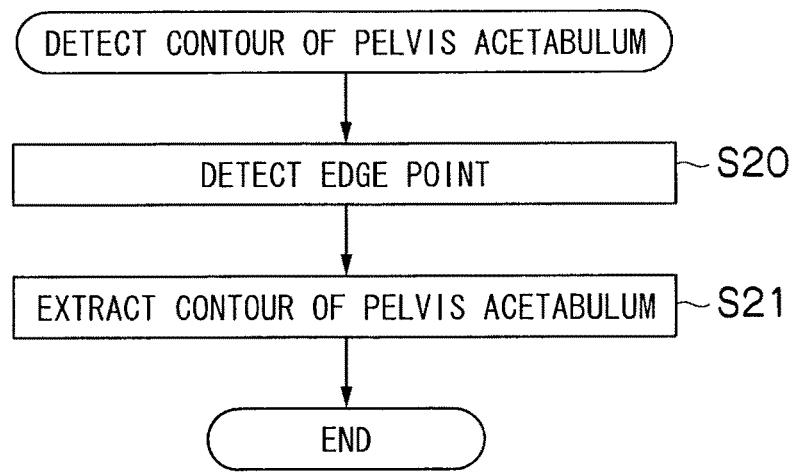
FIG. 9 is a flowchart showing a process of a method for detecting a contour of a pelvis acetabulum.

FIG. 9 is a flowchart showing a flow of the process of the method for detecting the contour of the pelvis acetabulum. Further, FIG. 10 is an explanatory view showing the example of edge detection of the pelvis acetabulum.

First, in step S20 of FIG. 9, edge point detection is performed.

Figure 10A:
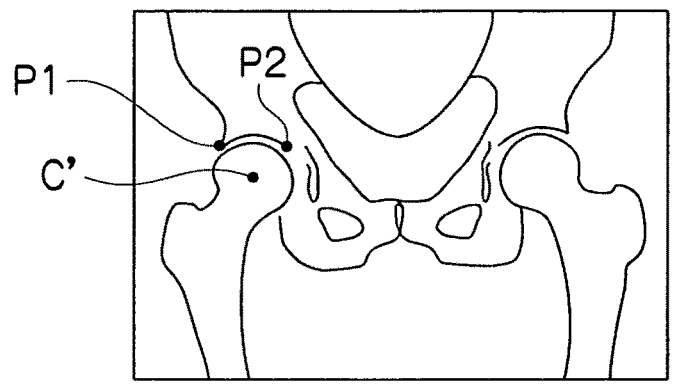
FIGS. 10A to 10C are explanatory views showing an example of edge detection of a pelvis acetabulum.

In concrete, first as shown in FIG. 10A, as input information, a substantial center C' of the thigh femoral head (femoral head center candidate point) and an outer end P1 of a hip cup and an inner end P2 of a hip cup are inputted as above.

Figure 10B:
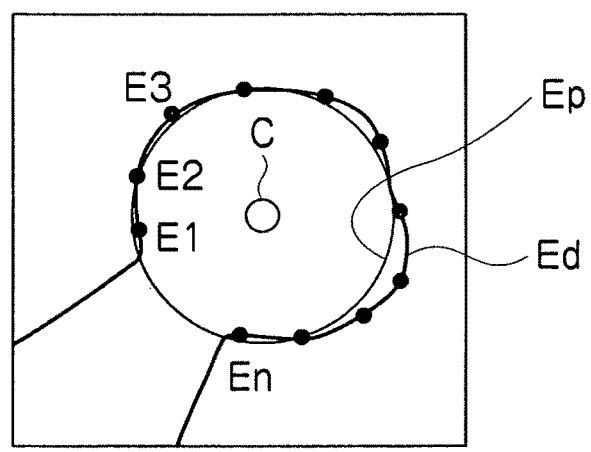

Next, as shown in FIG. 10B, an image with a thigh femoral head portion being enlarged is displayed, a plurality of edge candidate points E1, E2, E3, . . . , En are taken on the perimeter Ed of the femoral head (portion which seems to be an edge), and an ellipse (approximation ellipse) Ep which includes as many of these points as possible on the perimeter is obtained. For this, as described above, the formula of the ellipse is expressed by using the parameters such as the coordinates of the center of the ellipse, the long axis, the short axis, and the angle of rotation around the center, and by using the coordinates of each of the edge candidate points and the expression of the ellipse, the evaluation value expressing the degree of approximation of the ellipse to the edge candidate points is calculated from the distance of the ellipse and the edge candidate points and the like, the parameters are changed, and the ellipse by which the evaluation value becomes the maximum is set as the ellipse for approximating the edge of the thigh femoral head.

When the ellipse for approximating the edge of the thigh femoral head is determined like this, the center of the approximation ellipse is set as the thigh femoral head center C again.

Figure 10C:
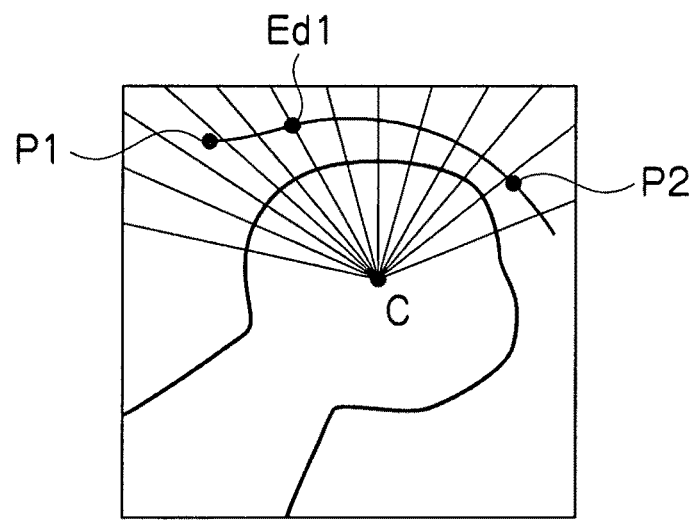

Next, as shown in FIG. 10C, straight lines are radially drawn between the outer end P1 of the hip cup and the inner end P2 of the hip cup upward from the femoral head center C, and by searching the points at which the density of each pixel changes from high to low along the straight lines, the edge point Ed1 of the pelvis acetabulum is detected.

Next, in step S21 of FIG. 9, the contour of the pelvis acetabulum is extracted.

Figure 11:
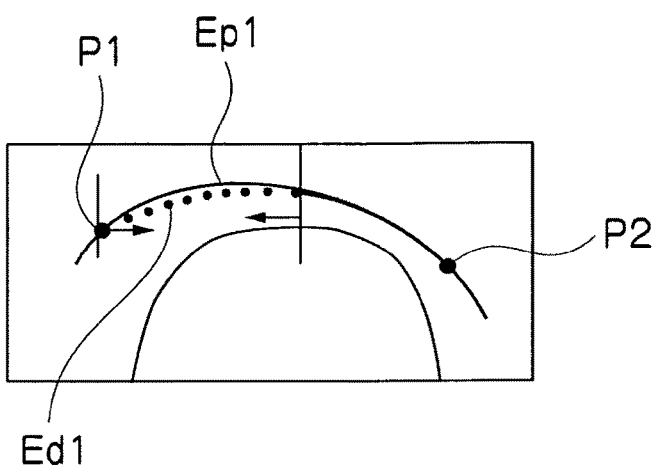
FIG. 11 is an enlarged view showing a pelvis acetabulum and a thigh femoral head portion.

FIG. 11 shows portions of the pelvis acetabulum and the thigh femoral head by enlarging them.

Since the edge points Ed1 of the pelvis acetabulum are detected above, the contour of the pelvis acetabulum is obtained by approximating these edge points Ed1 by the ellipse Ep1.

The calculation method of the approximation ellipse Ep1 can be performed similarly to the one used when the thigh femoral head is approximated by the ellipse Ep above.

Next, the edge points on the circumference of the approximation ellipse Ep1 and in its vicinity are searched.

Subsequently, the range where the edge points Ed1 are continuously present on the circumference of the approximation ellipse Ep1 is determined as the portion which can be approximated by the approximation ellipse Ep1, and the circumferential shape of the approximation ellipse Ep1 is extracted as the contour of the pelvis acetabulum from the local region image on which the pelvis acetabulum comes out.

Meanwhile, the range which deviates from the circumference of the approximation ellipse Ep1, and in which the edge points Ed1 are continuously present in the vicinity of the circumference is determined as the portion which cannot be approximated by the approximation ellipse Ep1. Thus, as shown by the arrows in FIG. 11, from both ends of the range which deviates from the circumference of the approximation ellipse Ep1, and in which the edge points Ed1 are continuously present in the vicinity of the circumference, the edge points Ed1 which are continuously present are connected to one another toward the center of the range, and the shape formed by this is extracted as the contour of the pelvis acetabulum from the local region image on which the pelvis acetabulum comes out. In order to connect the edge points Ed1, a proper known interpolation method can be applied. The operation may be automatically performed, or may be semi-automatically performed by the instruction of a user.

When extraction of the contour of the pelvis acetabulum ends in failure, the point on the contour which should be originally passed is clicked, and thereby, the edge point Ed1 located at the position which is the nearest from the point is set as a relay point of the search range. Subsequently, with the region from both ends of the original search range to the relay point being set a new search range, the edge points Ed1 are connected toward the center.

The contour of the pelvis acetabulum is detected as above.

Here, returning to the flowchart of FIG. 2 again, the measurement range is set by the measurement range setting unit in step S3 of FIG. 2 next (measurement range setting step).

Figure 12:
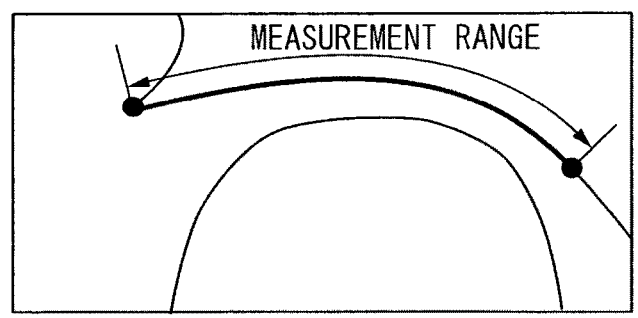
FIG. 12 is a view showing an example of setting the entire contour of the pelvis acetabulum to a measurement range.

As the measurement range, as shown in FIG. 12, for example, the entire contour of the pelvis acetabulum which is detected is set as the measurement range.

Figure 13:
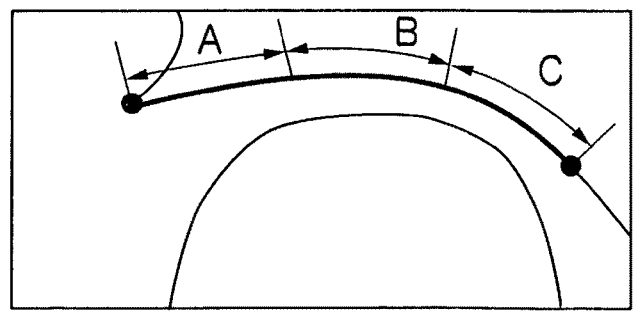
FIG. 13 is a view showing an example of dividing the contour of the pelvis acetabulum into a plurality of regions.

Further, as shown in FIG. 13, the detected contour of the pelvis acetabulum is divided into several regions (divided into three equal parts of an A region, a B region and a C region in FIG. 13), and all the divided regions are set as the measurement ranges. Alternatively, any of the divided regions is selected and set as the measurement range. For example, any one of the regions A (outer side), B (central portion) and C (inner side) of the detected contour of the pelvis acetabulum of FIG. 13, or the A region and B region, the B region and C region, and the A region and C region of the contour of the pelvis acetabulum of FIG. 13 are set as the space measurement range.

Figure 14:
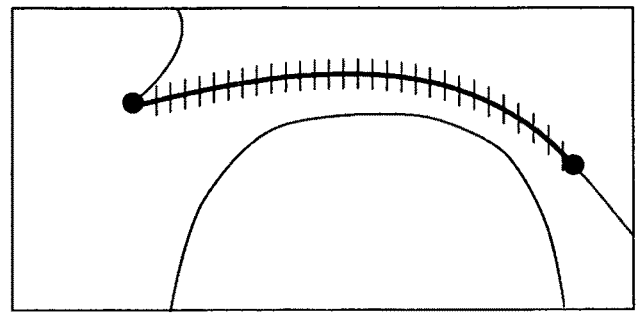
FIG. 14 is a view showing an example of the contour of the pelvis acetabulum into a number of small regions.

Further, as shown in FIG. 14, it is conceivable to divide the detected contour of the pelvis acetabulum into a number of small regions and set all the small regions as the measurement ranges.

The divided regions shown in FIGS. 13 and 14 are not limited to the case of being divided into equal parts, but may be divided into different parts for the respective regions. For example, experience shows that in the contour of the outer side of the pelvis acetabulum, advance extent of space narrowing and the evaluation value of the joint space are easily correlated, and therefore, it is conceivable to make the size of the A region larger than the sizes of the B region and the C region in FIG. 13.

Further, the number of divisions, the sizes of the respective divided regions, selection of the divided regions and the like may be determined in advance, or may be inputted or selected by the user by the information input unit 28 at each time.

Next, in step S4 of FIG. 2, the space width is calculated in the space width calculation unit 20 (space width calculating step). As the calculation method of the space width, calculation methods 1 to 3 are conceivable as follows.

(Calculation Method 1)

Figure 15:
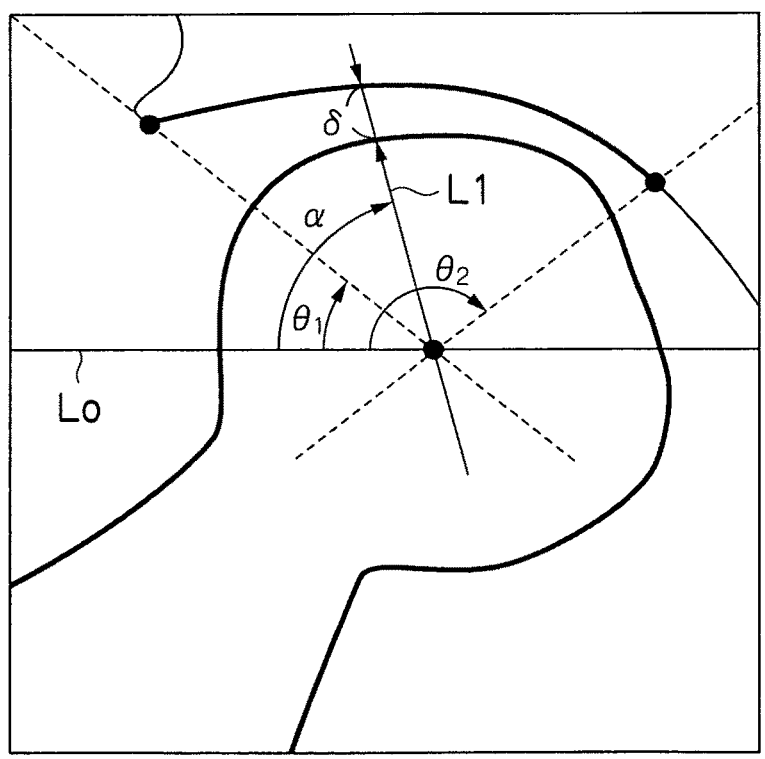
FIG. 15 is an explanatory view of a calculation method 1 of a space width.

FIG. 15 is an explanatory view of the calculation method 1 of the space width. As shown in FIG. 15, the intersection points of a straight line L1 passing through the thigh femoral head center, and the contour of the pelvis acetabulum (the contour in the range from the angles θ1 to θ2 with the thigh femoral head set as the center with the straight line L0 of FIG. 15 as the reference) and the thigh femoral head contour (at the side opposed to the pelvis acetabulum) are respectively obtained, and the distance between these intersection points is calculated as a space width δ. The straight line L1 is considered as a plurality of straight lines extending radially from the thigh femoral head center by changing an inclination α of the straight line L1 with respect to the straight line L0 within the aforementioned measurement range, and by calculating the space width δ with respect to each of the straight lines L1, serial data of the space width δ in the measurement range can be acquired. Hereinafter, the straight line L0 is a straight line which is parallel with a straight line La connecting the tear drop lower end points M and N shown in FIG. 3, and passes through the thigh femoral head center. Further, as the thigh femoral head center, the result calculated in the contour detecting step (step S2 of FIG. 2) is used.

(Calculation Method 2)

Figure 16:
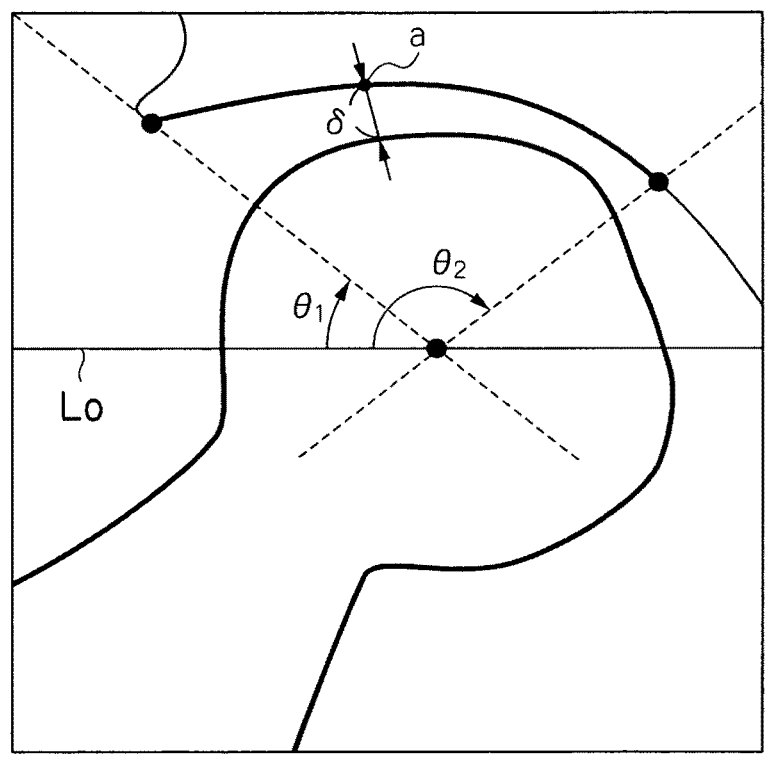
FIG. 16 is an explanatory view of a calculation method 2 of a space width.

FIG. 16 is an explanatory view of a calculation method 2 of the space width. As shown in FIG. 16, with respect to a point a on the contour of the pelvis acetabulum, the distance to the point on the thigh femoral head contour which is at the nearest position (the minimum distance from each point on the contour of the pelvis acetabulum to the thigh femoral head contour) is calculated as the space width δ. With respect to a plurality of points on the contour of the pelvis acetabulum, the distance to the point on the thigh femoral head contour which is at the nearest position is calculated as the space width δ within the aforementioned measurement range, and thereby, the serial data of the space width δ in the measurement range can be acquired.

(Calculation Method 3)

Figure 17:
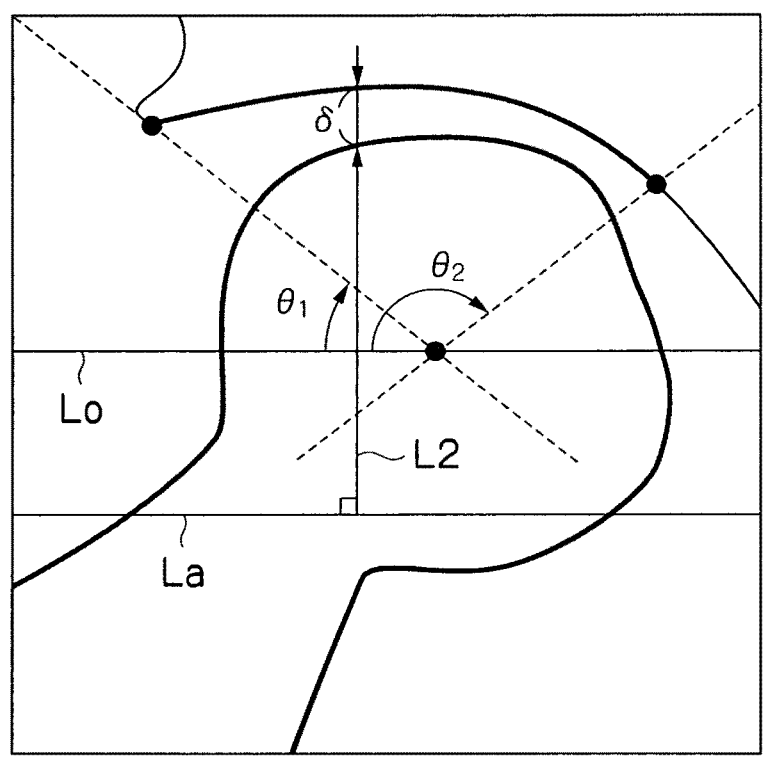
FIG. 17 is an explanatory view of a calculation method 3 of a space width.

FIG. 17 is an explanatory view of a calculation method 3 of the space width. As shown in FIG. 17, the distance between the intersection points of a line L2 at a predetermined angle which passes through the contour of the pelvis acetabulum and the thigh femoral head contour, and the contour of the pelvis acetabulum and the thigh femoral head contour (at the side opposed to the pelvis acetabulum) is calculated as the space width δ. Subsequently, the space width δ is calculated with respect to each point on the contour of the pelvis acetabulum within the aforementioned measurement range, and thereby, the serial data of the space width "δ" within the measurement range can be acquired. In FIG. 17, as one example of the line L2 at the predetermined angle which passes through the contour of the pelvis acetabulum and the thigh femoral head contour, the perpendicular (line parallel with the body axis) of the straight line La (see FIG. 3) connecting the tear drop lower end points "M" and "N" at both sides is used.

In addition, in the calculation methods 1 to 3, at least any one of the minimum value and the average value of the serial data of the space width δ within the measurement range may be calculated.

As above, the space width calculated by the calculation methods 1 to 3 expresses the distance between the pelvis acetabulum and the thigh femoral head, and therefore, is the evaluation value with which the advance extent of space narrowing can be objectively evaluated.

Further, in the calculation methods 1 to 3, out of the serial data of the space width δ which is obtained at each of the points on the respective straight lines L1 and L2 or the contour of the pelvis acetabulum, a neighborhood average space width "δave" which is an average value of an arbitrary space width δ and a plurality of space widths δ (neighborhood space widths) obtained in the neighborhood of it may be calculated. The range of the neighborhood which is taken into consideration to calculate the neighborhood average space width δave is desirably determined in advance.

Figure 18:
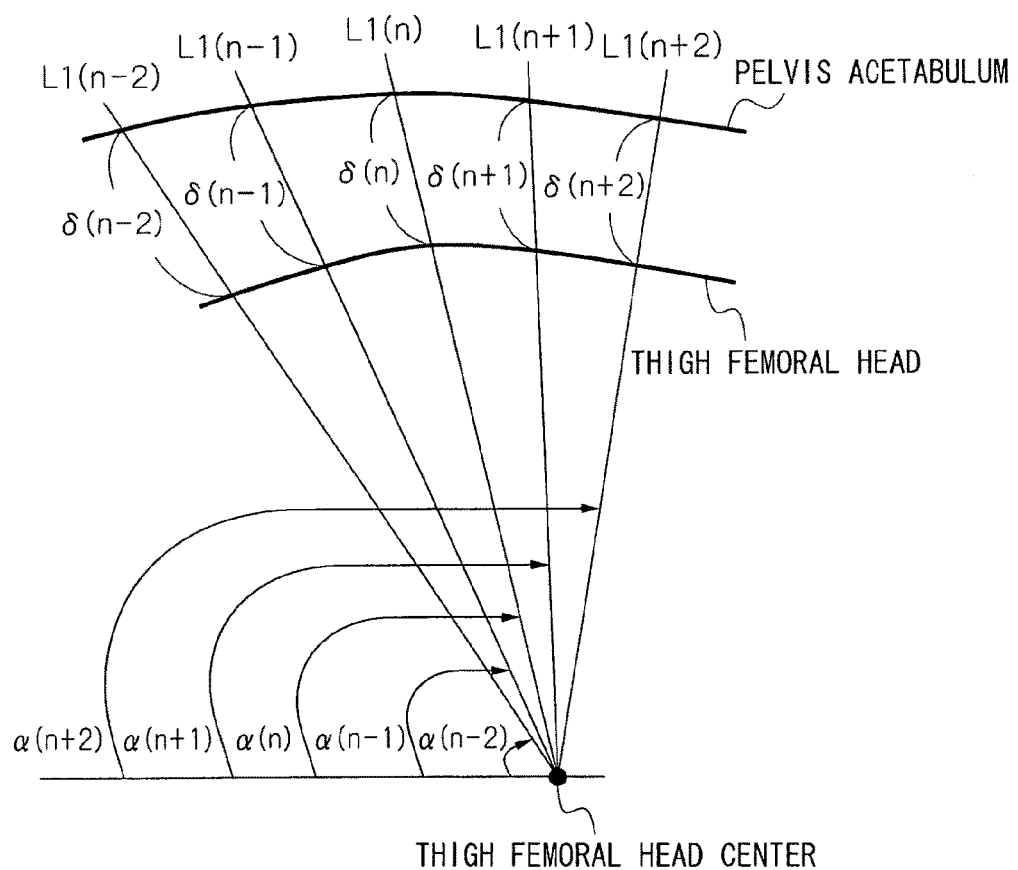
FIG. 18 is an explanatory diagram showing a space width in each straight line L1 in the calculation method 1 of the space width.

Thus, a concrete calculation method of the neighborhood average space width δave will be described hereinafter. Here, the method will be described with the calculation method 1 cited as an example. FIG. 18 is a view showing the space width in each straight line L1 in the calculation method 1 of the space width.

As shown in FIG. 18, as an example, the neighborhood range which is taken into consideration for calculating the neighborhood average space width δave is set as, for example, 5° (degree), and angles α(n−2), α(n−1), α(n), α(n+1) and α(n+2) are considered within the range. n is an integer which is 3 or larger. The straight lines at the respective angles are set as L1(n−2), L1(n−1), L1(n), L1(n+1) and L1(n+2), and as the respective space widths, δ(n−2), δ(n−1), δ(n), δ(n+1) and δ(n+2) are assumed to be calculated by the aforementioned calculation method 1.

Subsequently, the average value of the space widths δ(n−2) to δ(n+2) is calculated as the neighborhood average space width δave(n) in the straight line L(n). More specifically, the average value is expressed by the following Expression.

$$\delta\text{ave}(n) = \frac{\delta(n-2) + \delta(n-1) + \delta(n) + \delta(n+1) + \delta(n+2)}{5} \quad [\text{Expression 1}]$$

The number of angles within the neighborhood range which is taken into consideration for calculating the neighborhood average space width δave(n) is not limited to five, and can be optionally selected. Further, as the neighborhood range which is taken into consideration for calculating the neighborhood average space width δave, the range of 10 mm on the contour of the pelvis acetabulum, for example, is conceivable in the calculation method 2 and the calculation method 3, but the range is not especially limited to this length.

By calculating the space width as the neighborhood average space width δave like this, the influence of noise on the image is not received, and the serial data of the space width can be prevented from becoming the minimum locally due to the influence of noise.

Further, the neighborhood range which is taken into consideration for calculating the neighborhood average space width δave can be determined based on the characteristic of the noise on the image. For example, it is assumed to be statistically obvious that spike noise occurs at every 2 mm due to the influence of scattered radiation. At this time, some variation of the noise generation position is taken into consideration, and it is conceivable to set the neighborhood range which is taken into consideration for calculating the neighborhood average space width δave at 4 mm.

Further, when the minimum space width within the measurement range is calculated based on the neighborhood average space width δave, the contrivance as follows is conceivable.

As described above, with respect to the space width at each of the straight lines L1 and L2, or each point a, the neighborhood average space widths δave are calculated in all the straight lines or points. However, this also takes much time when only the minimum space width (minimum neighborhood average space width δave) within the measurement range is desired to be calculated. Thus, a predetermined number (for example, three) of the space widths δ are extracted in the order of the value, the smallest, the first, in the space widths δ in the respective straight lines L1 and L2 or the respective points a calculated by the calculation methods 1 to 3, and the neighborhood average space width δave is calculated with respect to only the predetermined number of extracted space widths δ. It is conceivable to set the minimum value out of the calculated neighborhood average space widths δave as the minimum space width within the measurement range.

Here, δave is obtained, but in order to reduce the influence on the minimum space width measurement by noise, the other statistic processing methods may be used. For example, a method for defining the central value δmed of δ(n−2), δ(n−1), δ(n), δ(n+1) and δ(n+2) as the minimum space width in the straight line L(n) and the like are conceivable.

The space width calculating step is described above, and the calculation methods 2 and 3 also can be applied to the joints (knee joint, an elbow join and the like) other than a hip joint.

Next, in step S5 of FIG. 2, the calculation result of the space width δ is displayed (calculation result display step). The calculation result of the space width δ (serial data) is subjected to predetermined image processing and is displayed on the display screen of the display unit 32.

Hereinafter, the display method of the calculation result will be described.

As the examples of display of calculation result, for example, display examples 1 to 3 which will be described hereinafter are conceivable first as the ones that simply display the result which is obtained from the image which is read at present. The calculation result may be displayed by optionally combining display examples 1 to 3.

Figure 19A:
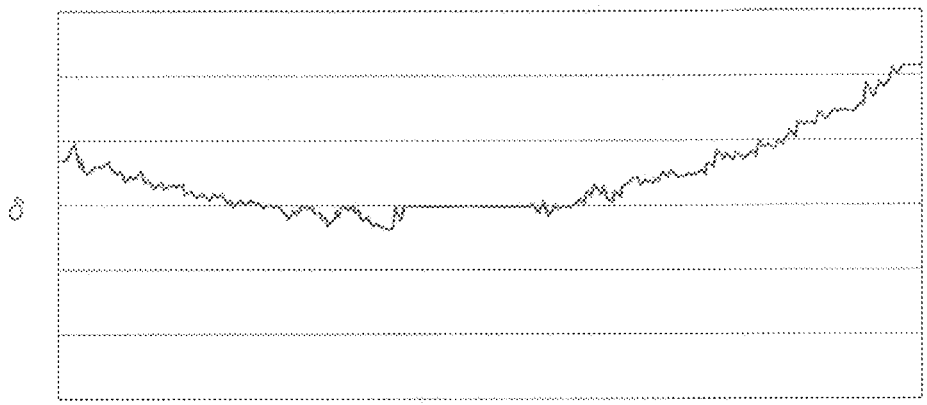
FIGS. 19A and 19B are explanatory diagrams of a display example 1 of a result of calculation.
Figure 19B:
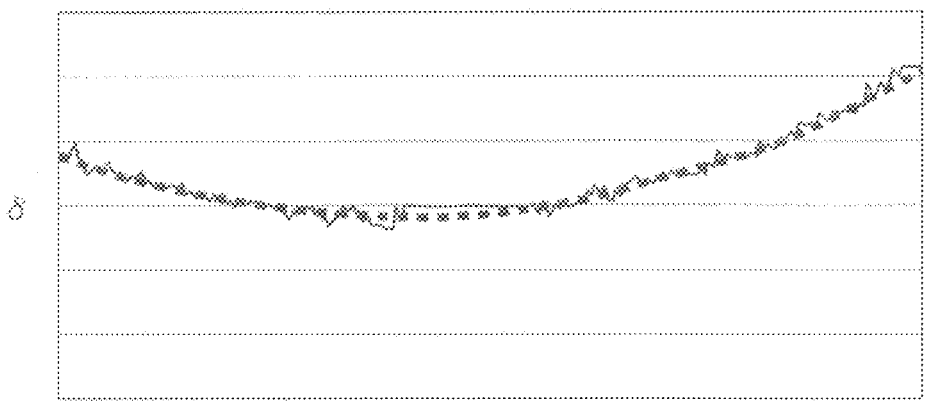

FIGS. 19A and 19B are explanatory diagrams of the display example 1 of the calculation result. As shown in FIG. 19A, the serial data of the space width δ is graphically displayed. For example, as shown in FIG. 19A, the serial data is graphically displayed by plotting the position on the contour of the pelvis acetabulum on the axis of abscissas, and plotting the space width δ calculated by the calculation methods 1 to 3 on the axis of ordinates.

When the contour of the pelvis acetabulum is divided into a number of small regions and all the small regions are set as the measurement ranges in the measurement range setting step (step S3 of FIG. 2) (FIG. 14), the range of the axis of abscissas is set as the entire contour of the pelvis acetabulum, and the axis of ordinates may be expressed as the average value or the minimum value of the space width δ in each of the measurement ranges, which is calculated by the calculation methods 1 to 3.

Further, as shown in FIG. 19B, the serial data (shown by the broken line in the drawing) of the neighborhood average space width δave calculated as above may be displayed by being superimposed. As shown by the broken line in FIG. 19B, the serial data of the neighborhood average space width δave draws a smooth curve, and therefore, the state of the space width in each portion on the contour of the pelvis acetabulum is easily grasped.

FIGS. 20A and 20B are explanatory diagrams of the display example 2 of the calculation result. As shown in FIG. 20A, the minimum value and the average value of the serial data of the space width δ (or the neighborhood average space width δave) within the above measurement range are displayed. When the divided ranges which are the result of dividing the contour of the pelvis acetabulum into several ranges are set as the respective measurement ranges in the measurement range setting step (FIG. 13), the minimum value and the average value of the serial data of the space width δ (or the neighborhood average space width δave) of each divided range may be displayed as shown in FIG. 20B. Further, only the minimum value or only the average value of the serial data of the space width δ (or the neighborhood average space width δave) may be displayed.

Figure 21:
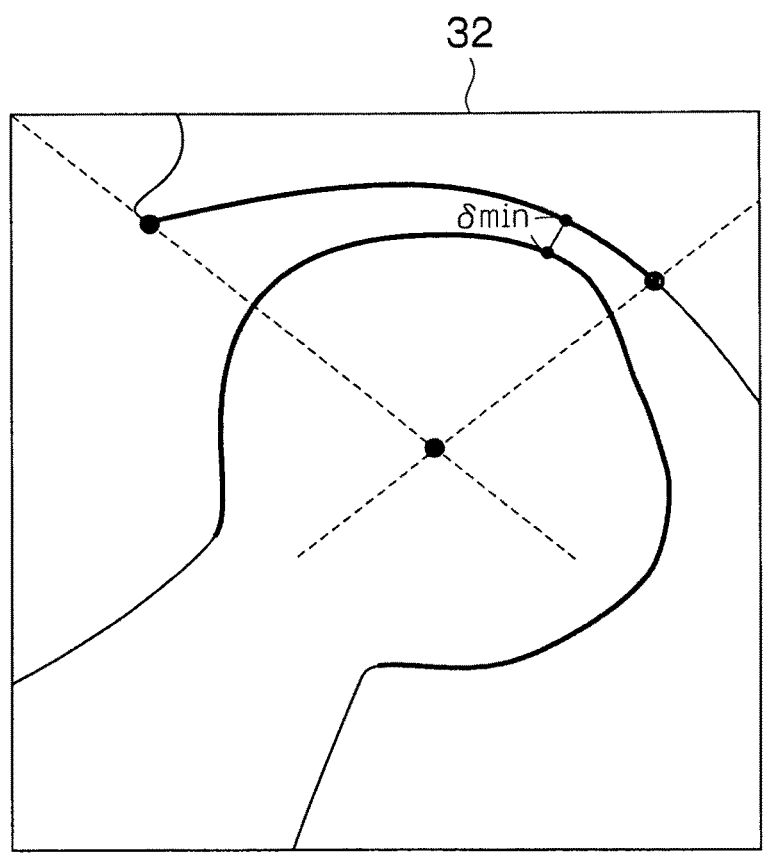
FIG. 21 is an explanatory view of a display example 3 of a result of calculation.

FIG. 21 is an explanatory view of the display example 3 of the calculation result. As shown in FIG. 21, the enlarged image of the portions of the pelvis acetabulum and the thigh femoral head is displayed on the display unit 32, and the contour of the pelvis acetabulum and the thigh femoral head contour detected in the enlarged image, the portion of the minimum space width δmin which is the minimum value of the serial data of the space width δ (or the neighborhood average space width δave) within the above measurement range, and the like are displayed by being emphasized.

Further, the display method of the evaluation value may be switched in accordance of the evaluation value of the space width δ. For example, it is conceivable that when the minimum space width has a value less than a predetermined value (1 mm), the color of the corresponding portion in the graph shown in FIG. 19 is changed, the color, thickness, font and the like of the characters of the evaluation value (minimum value and the average value) of the space width δ (or the neighborhood average space width δave) shown in FIG. 20 are changed, or the color and the thickness of display of the contour of the pelvis acetabulum and the thigh femoral head contour, and the space width δ are changed in the enlarged image of the portions of the pelvis acetabulum and the thigh femoral head shown in FIG. 21.

Further, when the graphs shown in FIGS. 19A and 19B, and the enlarged image of the portions of the pelvis acetabulum and the thigh femoral head shown in FIG. 21 are displayed on the display unit 32, by clicking arbitrary points in the graph shown in FIGS. 19A and 19B, the contour portion of the pelvis acetabulum and the contour portion of the thigh femoral head which correspond to the points in the enlarged image shown in FIG. 21 may be displayed by being emphasized.

Figure 22:
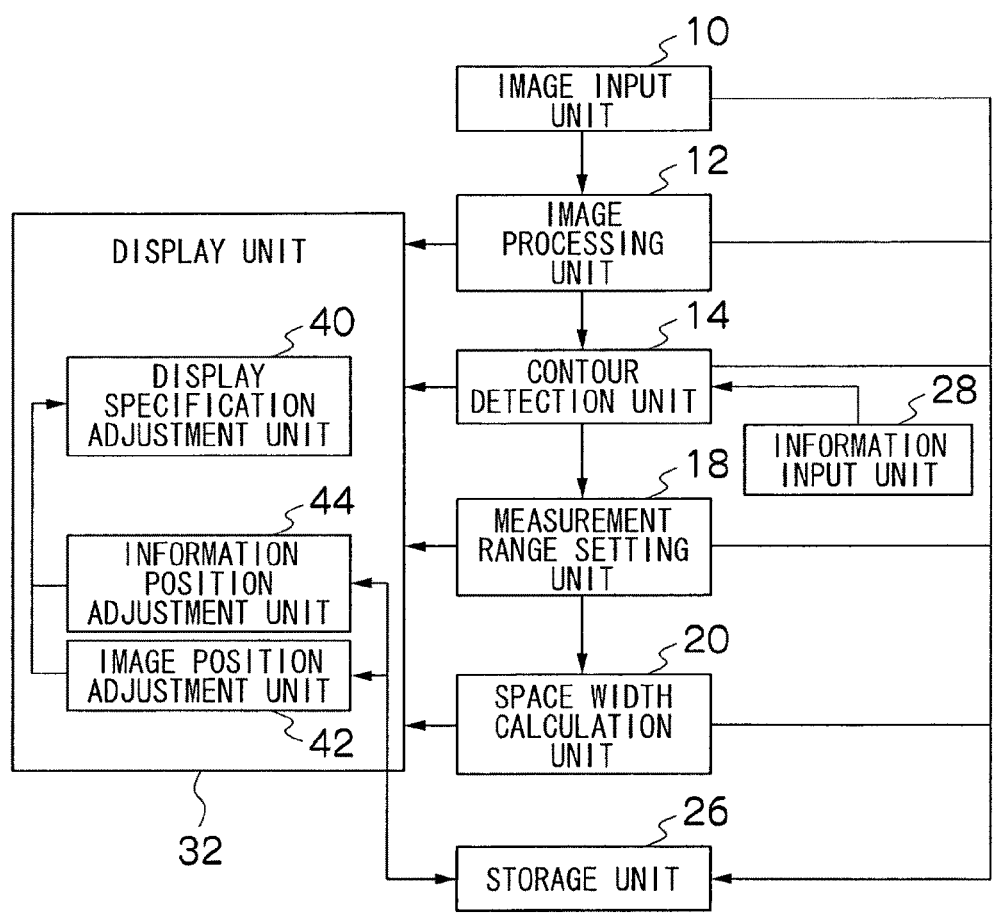
FIG. 22 is a block diagram of a system for measuring space width of joint showing a configuration of a display unit.
Figure 23:
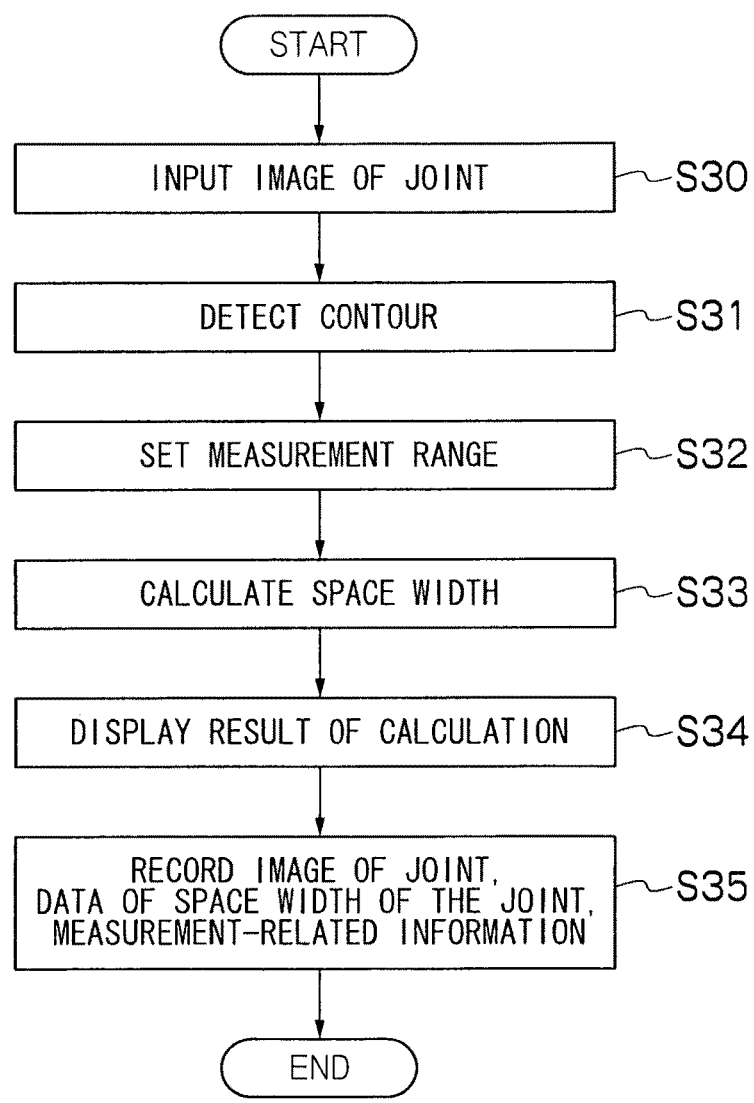
FIG. 23 is an overall flowchart of a process of measuring space width of joint, the process further including a recording step.

Further, as shown in FIG. 22, the system 1 for measuring space width of joint of the presently disclosed subject matter has the storage unit 26. FIG. 22 displays the system configuration by partially omitting it. As shown in FIG. 23, the image of the joint inputted in the aforementioned joint image inputting step (hereinafter, called a joint image) is stored (recorded) in the storage unit 26 (recording step of step S35 of FIG. 23).

Further, at the same time, the data of the space width δ calculated in the space width calculating step, and the measurement-related information in each step are also stored in the storage unit 26. Here, the measurement-related information includes, for example, a contour line detected in the contour detecting step, a measurement range set in the measurement range setting step, a space width calculated in the space width calculating step, the measuring position of the space width and the like, in addition to which, the coordinate information of the femoral head center point, a tear drop lower end, and acetabular end point and the like used in each of the steps, drawing information used in each of the steps, a sketch, note and the like of a user (a doctor or the like) and the like.

As one example of the storage unit 26, a database which accumulates and stores interpretation of radiogram report, electronic medical record and the like included in a system for managing medical information such as a PACS (Picture Archive and Communication system) is conceivable.

The radiogram interpretation report is an electronic file which is created by describing the result of diagnosis of a doctor or the like as a comment, in which a joint image used for diagnosis is incorporated.

The data of the space width δ and the measurement-related information are recorded together when the corresponding joint image is recorded, and the identification information with which the relation with the corresponding joint image can be recognized is recorded and stored. For example, as the recorded information file including the data of the space width δ and the measurement-related information, creation of the recording information file with the same name as the file name of the image file of the corresponding joint image is conceivable. Further, the name of the image file of the corresponding joint image may be written to the header portion of the recording information file.

Separately from the recording step of step S35 of FIG. 23, the storage unit 26 also records the positioning information of the image which will be described later.

Figure 24:
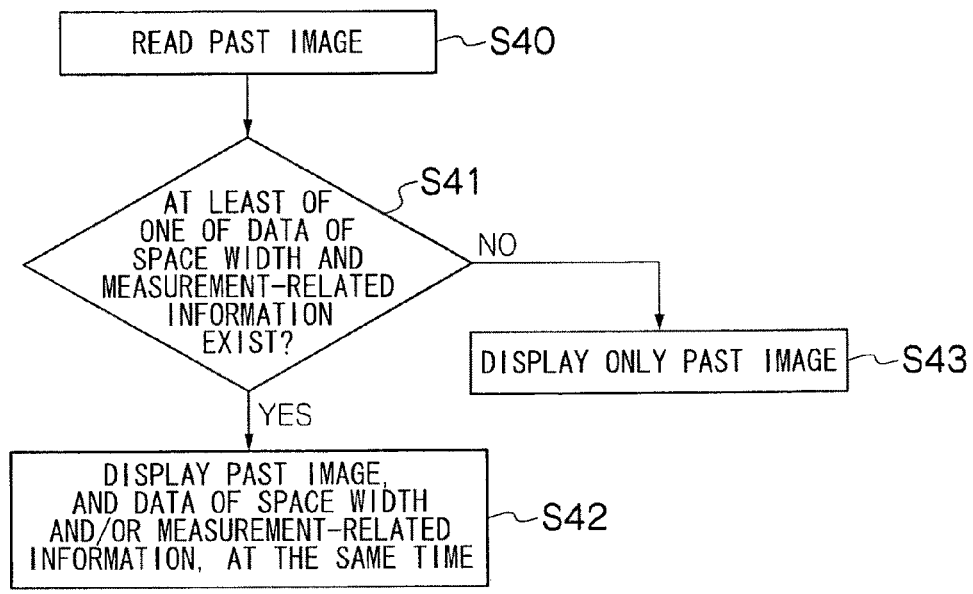
FIG. 24 is a flowchart showing reading processing of a past image of the joint.

The past joint image which is stored in the storage unit 26 as described above can be read again and displayed on the display unit 32 (the past image reading step of step S40 of FIG. 24).

When the data of the space width δ and the measurement-related information corresponding to the image of the joint are stored with the image of the joint at this time, the data of the space width δ and the measurement-related information can be simultaneously read and displayed on the display unit 32 (the past image display step of steps S41 and S42 of FIG. 24). Thereby, even if measurement is not performed again with respect to the past joint image, for example, the contour line, the space width δ and the like can be displayed.

If the data of the space width δ corresponding to the read past joint image and the measurement-related information are not stored, only the past joint image is displayed (the past image display step of steps S41 and S43 of FIG. 24).

Further, it is conceivable that while the past joint image stored in the storage unit 26 is read and displayed on the display unit 32, the present joint image which is inputted at present is also displayed on the display unit 32 as follows (the plurality of images display step).

More specifically, when the present joint image is displayed on the display unit 32, the past joint image is read from the storage unit 26 and displayed, and when the past joint image is read from the storage unit 26 and displayed on the display unit 32, the present joint image is displayed.

The specifications of display are adjusted by a display specification adjustment unit 40 (see FIG. 22), and the specification for displaying the past joint image and the present joint image on the display unit 32 by superimposing them on each other, the specification for displaying the past joint image and the present joint image on the display unit 32 by switching them, the specification for displaying the past joint image and the present joint image on the display unit 32 by arranging them side by side and the like are conceivable. These display specifications can be optionally switched at any time by a user operating a switching device (not illustrated).

When an image is displayed in the aforementioned plurality of images display step, positioning for adjusting the positions, angles, magnification ratios and the like of the past joint image and the present joint image so that they are displayed to be substantially equal on the display unit 32 is performed by an image position adjustment unit 42 (see FIG. 22).

In the specifications for displaying the past joint image and the present joint image by superimposing them on each other on the display unit 32, positioning is performed so that the past joint image and the present joint image are substantially superimposed on each other. Further, in the specifications for displaying the past joint image and the present joint image on the display unit 32 by switching them, positioning is performed so that when the image is switched, the image is displayed in substantially the same position and orientation at the same magnification ratio (size). Further, in the specifications for displaying the past joint image and the present joint image on the display unit 32 by arranging the images side by side, positioning is performed so that both the images are displayed with substantially the same height in substantially the same orientation at substantially the same magnification ratio (size).

Figure 25:
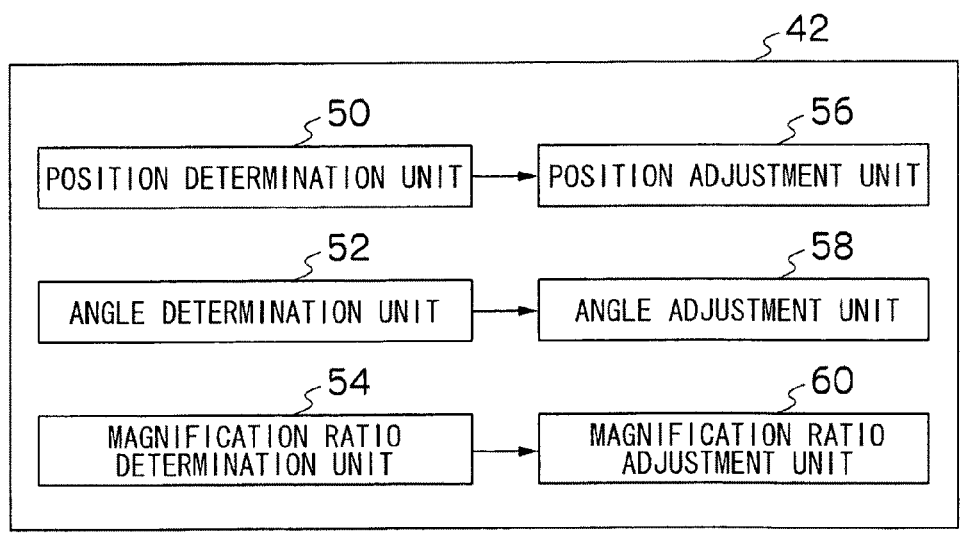
FIG. 25 is a block diagram of an image position adjustment unit.

The image position adjustment unit 42 includes, as shown in FIG. 25, a position determination unit 50 which determines the relative positions of a plurality of images to be positioned, an angle determination unit 52 which determines the relative angles, a magnification ratio determination unit 54 which determines the relative magnification ratios and the like.

The image position adjustment unit 42 also includes a position adjustment unit 56 which adjusts the relative positions of a plurality of images based on the positions determined by the position determination unit 50, an angle adjustment unit 58 which adjusts the relative angles of a plurality images based on the angles determined by the angle determination unit 52, and a magnification ratio adjustment unit 60 which adjusts the relative magnification ratio of a plurality of images based on the magnification ratio determined by the magnification ratio determination unit 54.

Thus, when the positioning information for performing positioning of the images as described above is already stored in the storage unit 26, the display unit 32 performs positioning of the image by acquiring the positioning information from the storage unit 26 and displays the image.

Meanwhile, when the positioning information is not stored in the storage unit 26, the display unit 32 automatically performs positioning of the image, and displays the image.

Further, when the positioning information is not stored in the storage unit 26, or when the positioning information is improper, positioning of the image is manually performed, and the image can be displayed. For example, a user performs operations of moving an image to a proper position by dragging the image on the screen of the display unit 32, enlarging and reducing the image to a proper size by a mouse wheel or the like, changing the orientation of the image to a proper orientation by turning the image by dragging the end point of the image and the like. An exclusive screen (small window or the like) for manually positioning the image like this may be included within the screen of the display unit 32, or separately from the display unit 32, and positioning of the image may be performed by using the exclusive screen.

The positioning information which is set when positioning of the image is automatically or manually performed like this is stored in the storage unit 26.

The concrete record contents of the positioning information include, for example, the relative positional relationship of predetermined points (points at four corners and the like) with respect to a certain coordinate point on the screen (a plurality of points such as end points of the screen may be adoptable), the angle with respect to a certain coordinate axis on the screen, the magnification ratio with respect to the size of the coordinate region on the screen (for example, the number of pixels on the screen) and the like.

Other than the above, the concrete record contents of the positioning information includes the relative positional relationship of a predetermined point of the image at the positioning side (a plurality of points such as points at four corners may be adoptable) with respect to the predetermined points (points at four corners and the like) of the image to be the reference of positioning. Alternatively, the relative angle of an arbitrary side in the outer perimeter of the image at the positioning side with respect to an arbitrary side in the outer perimeter of the image to be the reference of positioning is cited. Alternatively, the magnification ratio (for example, the relative value of the number of pixels on the screen) of the size of the image at the positioning side with respect to the size of the image to be the reference of positioning and the like are conceivable.

When positioning is performed when the past joint image and the present joint image are displayed by being superimposed on each other, positioning is considered to be performed with the acetabular contour, the femoral head contour, the femoral head center point, the tear drop lower end, the acetabular end point, the entire pelvis, or the position of combination of them as the reference. Further, the contour lines of the acetabular contour and the femoral head contour, the feature points and the like in the past joint image and the present joint image are automatically detected, and positioning may be automatically performed based on this detection result.

Further, in the aforementioned plurality of images displaying step, in addition to the past joint image and the present joint image, the aforementioned measurement-related information is also positioned by an information position adjustment unit 44 (see FIG. 22), and may be displayed on the display unit 32. The measurement-related information includes the data of the space width δ, the contour lines, measurement ranges, arbitrary points on the joint regions used for measurement, drawing information of the approximation ellipse or the like in the past joint image and the present joint image and the like, as described above.

Figure 26A:
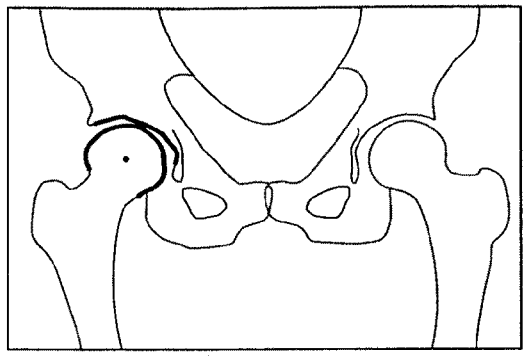
FIGS. 26A to 26C are views showing an example of displaying a present hip joint image and a past hip joint image by superimposing them on each other with a position of a thigh femoral head center as a reference.
Figure 26B:
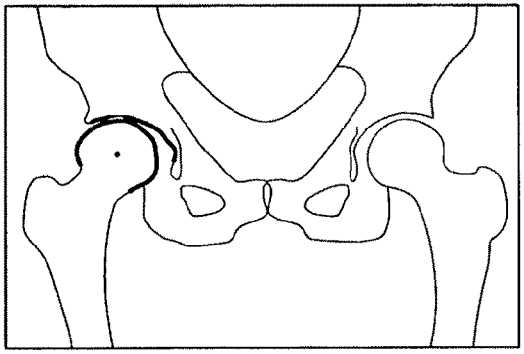
Figure 26C:
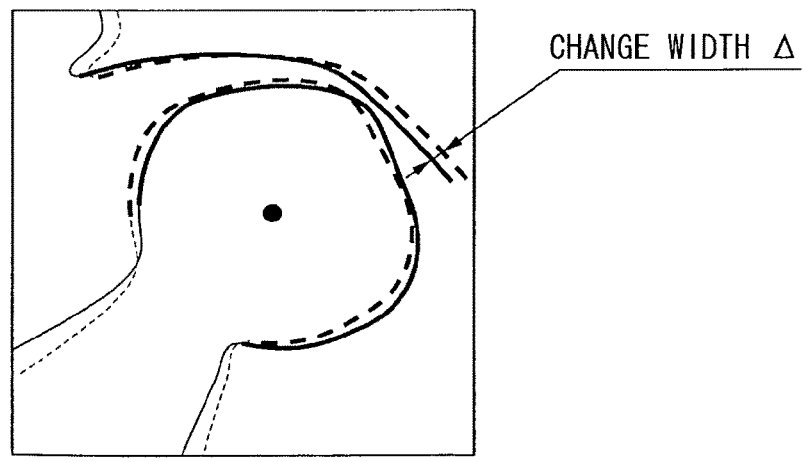

Here, FIG. 26C shows an example of displaying both images by superimposed them on each other with the position of the thigh femoral head center as the reference, when a hip joint is cited as an example, and the contours of the pelvis acetabulum in the present hip joint image (see FIG. 26A) and the past hip joint image (see FIG. 26B) are displayed by being superimposed on each other. As shown in FIG. 26C, the centers of the thigh femoral head are superimposed on each other by the image position adjustment unit 42 and the information position adjustment unit 44, and the magnification ratios of both the images are further matched with each other. Based on the magnification ratio, the contour lines in the present hip joint image and the past hip joint image, and the past joint image and the present joint image are deformed, and displayed by being superimposed on one another.

When the magnification ratios of the present hip joint image and the past hip joint image are matched with each other, one or more of the information of the acetabular contour, the femoral head contour, the femoral head center point, the approximation ellipse of the femoral head, and the acetabular end point out of the aforementioned measurement-related information is or are used, but use of the information of the femoral head center point and the femoral head contour is the most desirable.

Thereby, change of the past and present space widths can be easily observed from the change width Δ in the drawings, and the advance extent of the disease can be determined. For convenience of description, the present hip joint image is shown by the solid line, and the past hip joint image is shown by the broken line in FIG. 26C, and the display method is not limited to this.

Subsequently, the positioning information such as the relative position, the relative orientation and the magnification ratio on the screen of a plurality of pieces of measurement-related information which is used when a plurality of pieces of measurement-related information are positioned and displayed on the display unit 32 is also stored in the storage unit 26.

Further, any one of the past measurement-related information and the present measurement-related information is displayed in semi-opaque, and may be displayed by being superimposed on the other. When the measurement-related information is displayed in semi-opaque, it is conceivable to perform processing so that any one of the past measurement-related information and the present measurement-related information automatically becomes translucent at the time of being displayed on the display unit 32. Further, with respect to the past measurement-related information and the present measurement-related information displayed on the display unit 32, the measurement-related information to be made semi-opaque may be switched optionally by a user performing operation on the screen of the display unit 32. Further, whether each of the measurement-related information of the past and the present displayed on the display unit 32 is displayed in semi-opaque or not may be made individually selectable by a user performing operation on the screen of the display unit 32.

Further, display and non-display of the data of the space width δ and measurement-related information may be made switchable. Display and non-display may be made switchable for each item included in the measurement-related information such as the contour line, the measurement range of the space width, measurement position of the space width, and a sketch and a write of a user (a doctor or the like).

Further, a plurality of past joint images can be displayed by being superimposed in sequence, can be displayed by being switched, and can be displayed by being arranged side by side. At this time, for example, the image of the joint at the first medical examination may be preferentially displayed. Further, by clicking the screen, the next joint image may be displayed by being superimposed on the first image in sequence, may be displayed by being switched, and may be displayed side by side. Further, based on the measurement-related information such as the photographing date, the display sequence of a plurality of past joint images can be changed. Further, the measurement-related information such as a photographing date, pre-operation and post-operation is displayed by being listed, and a preferable image corresponding to the measurement-related information may be made selectable.

Further, the display sequence of a plurality of past joint images may be made presettable by a user. For example, the sequence of display for pre-operation and post-operation, the sequence of display for process observation and the like may be made settable optionally by a user as initial setting (default).

Further, a plurality of past joint images may be made displayable collectively by being superimposed on one another at one time. At this time, the color of each of the entire image may be gradually changed in sequence of the date of photographing. Thereby, the transition from the past with respect to the shape of the joint portion is known. Especially based on the measurement-related information of each of the images, the color of the contour line portion may be gradually changed in sequence of the photographing date. Thereby, the transition from the past is known especially with respect to the shape of the contour line.

Further, the screen of the display unit 32 is automatically divided in accordance with the number of the past joint images to be displayed, and a plurality of past joint images may be displayed by being arranged side by side on each of the divided screens. Thereby, the time and efforts of the user can be omitted when displaying a plurality of images by arranging them side by side so that the images are not superimposed on one another on the screen when the number of images becomes large.

Further, when the present joint image and the past joint image are displayed, and when a plurality of past joint images are displayed, the information of the photographing date, the number of photographing times, pre-operation and post-operation, and the like may be displayed so that each of the images can be discriminated on the screen.

Further, when the image of the joint is displayed on the display unit 32, the optical density contrasts may be matched by using the pixel value information of the region near the contours such as the acetabular contours and the femoral head contour in the past and present joint images (optical density contrast matching step). The optical density contrast may be matched based on the pixel information in the predetermined range in the periphery of the contour of the pelvis acetabulum of a hip joint and the thigh femoral head contour, for example. Further, the optical density contrast may be matched by using the information of the region other than the hip joint region. More specifically, the optical density contrast is matched with only the information of the portion which does not change.

Next, a display method will be described, in which the past image and the present image (or the past images) are compared, the related places are brought into correspondence with each other in a plurality of images and displayed together with the space width, and are made available for use in diagnosis of the advance extent and the like of the disease.

Figure 27:
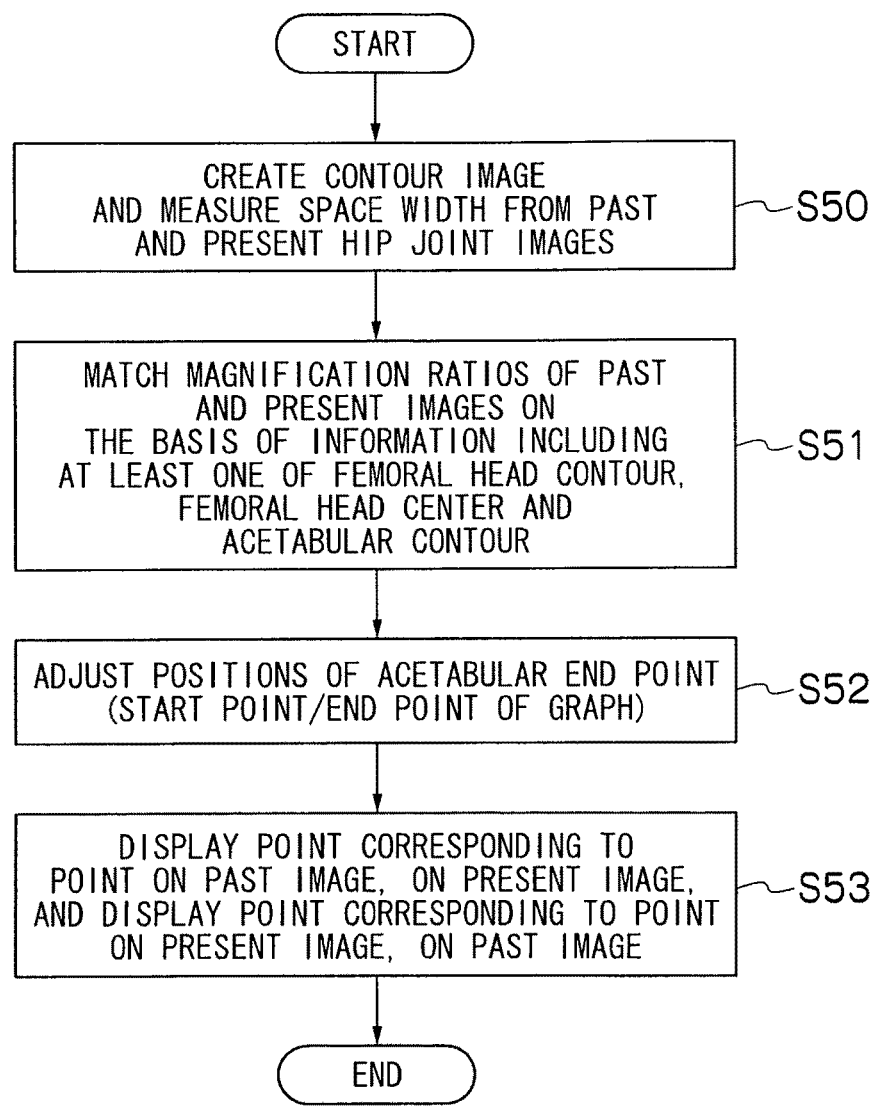
FIG. 27 is a flowchart showing a process of a first display method concerning display of a measurement result of a space width of a joint.

First, a first display method for displaying the joint space width measurement results of the past and the present by bringing them into correspondence with each other will be described. FIG. 27 shows the flow of the process of the first display method for display by bringing the past and the present results into correspondence with each other by a flowchart.

In step S50 of FIG. 27, by the aforementioned method, the contour image is created in the contour image forming unit 22 and the space width is measured (calculated) in the space width calculation unit 20, from the hip joint images obtained by radiographing the same patient in the past and the present (see FIG. 1).

More specifically, from both images of the present and the past, the femoral head contour, the femoral head center and the contour of the hip cup (acetabular contour) are extracted, and the contour image with only the contours is created. At this time, the approximation ellipse of the femoral head and the end point of the hip cup (acetabular end point) are also extracted. Subsequently, the space width is measured in each of the images.

At this time, with respect to the past image, if the femoral head contour, the femoral head center, and the acetabular contour are already extracted, the contour image is created, the space width is measured, the space width graph is formed, and they are stored in the storage unit 26, these data can be only called from the storage unit 26. When only the past image is stored in the storage unit 26, only the past image is called, and processing of extraction and the like of the above described contours is performed by using this.

Next, in step S51, the magnification ratios of the past and the present images are matched by using the information of at least one of the femoral head contour, the femoral head center, acetabular contour and the like. More specifically, by using at least one of the pieces of information of the femoral head contour, the femoral head center, the acetabular contour, the approximation ellipse of the femoral head, the acetabular end point and the like, the magnification ratios of the past image and the present image are matched with each other. The size of the object (such as the femoral head, the hip cup and the bone) in the past image and that in the present image can be matched with each other. As the information used here, use of two of the femoral head center and the bone contour is preferable. Thereby, the original images of the past and the present and the contour images of them are transformed so as to have the same magnification ratio.

Figure 28A:
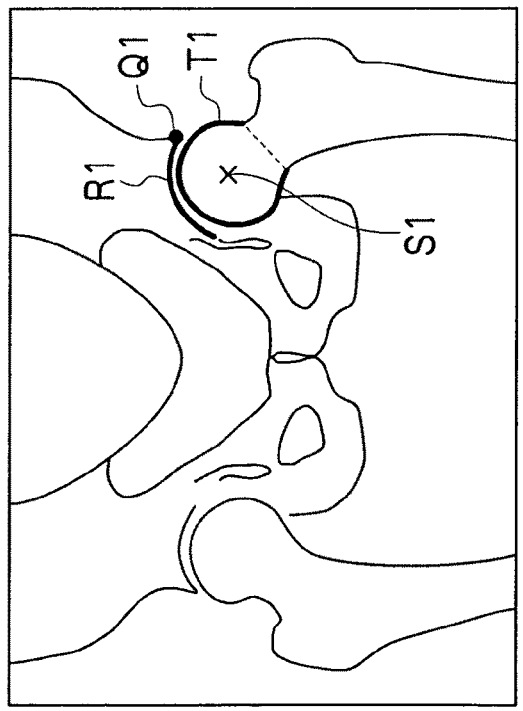
FIGS. 28A and 28B are explanatory views showing an example of original images of the past and present displayed on a display screen of the display unit.
Figure 28B:
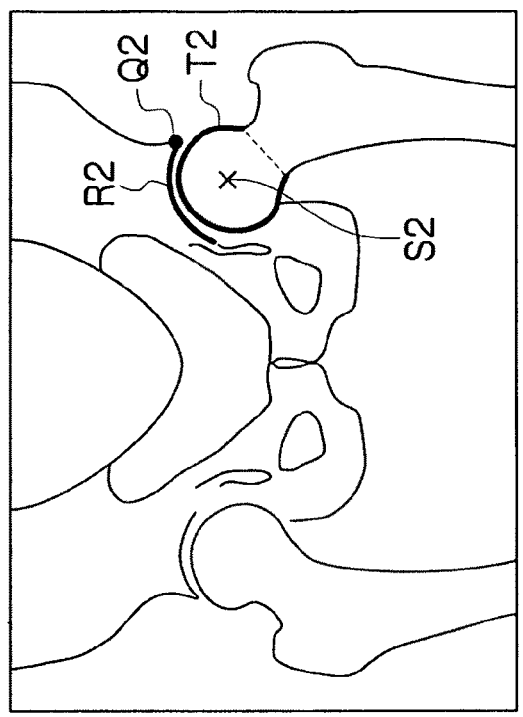

As shown in FIGS. 28A and 28B, the past and the present original images (a joint image or a contour image may be adoptable) are arranged at the left and the right, and are displayed on the display screen of the display unit 32. The extracted acetabular end points Q1 and Q2, acetabular contours R1 and R2, femoral head centers S1 and S2, and femoral head contours T1 and T2 are displayed on the past image and the present image.

In the present first display method, the past and the present images are displayed by being arranged side by side, and therefore, the images with the same magnification ratio are understandable at the time of comparison, but the magnification ratios do not necessarily have to be matched with each other.

Figure 29:
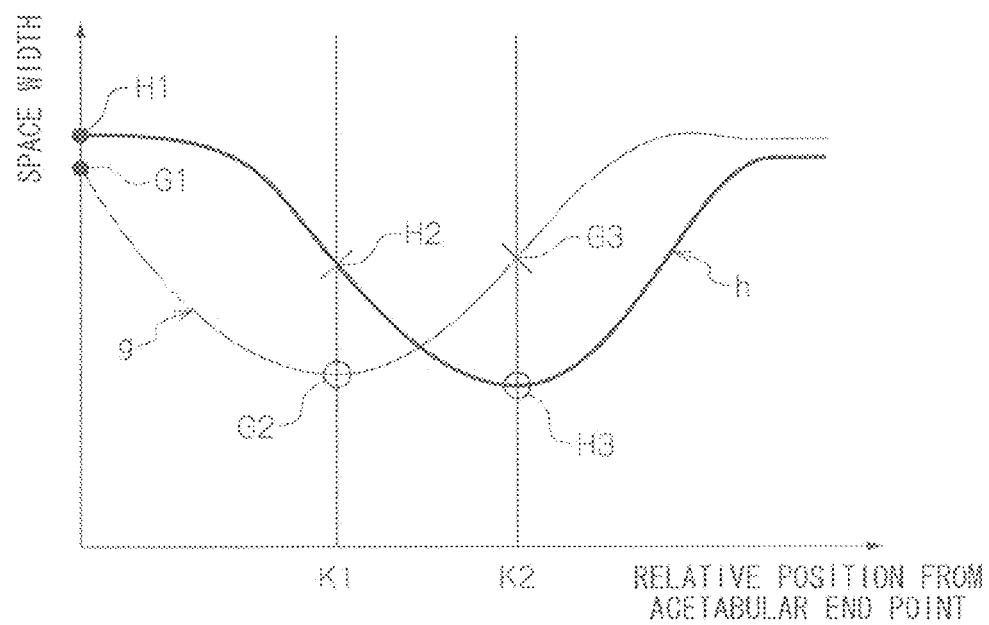
FIG. 29 is a chart showing an example of a space width graph in the first display method.

Next, in step S52, the acetabular end points Q1 and Q2 in FIGS. 28A and 28B are positioned as the start points when the space width graph is displayed. In the space width graph creating unit 24, the space width graphs of the past and the present are created, and the space width graph is displayed on the display screen of the display unit 32 as shown in FIG. 29. The space width graph may be displayed together with the images (original images or the contour images) of the past and the present, or may be displayed by being switched to them.

In FIG. 29, g represents a space width graph in the present image, and h represents a space width graph in the past image, the axis of abscissas represents a relative position from the acetabular end point along the acetabular contour in each of the present and the past images, and the axis of ordinates represents the value of the space width.

In FIG. 29, start points G1 and H1 of the space width graph g in the present image and the space width graph h in the past image correspond to the space widths in the acetabular end points Q1 and Q2 in FIGS. 28A and 28B, respectively. The end points of the space width graphs may be matched with each other, but they do no especially have to be matched, and the graphs may end at different positions, respectively.

In the space width graph of FIG. 29, in the present image, the space width becomes a minimum G2 at a relative position K1 from the acetabular end point, whereas in the past image, the space width becomes a minimum H3 at a relative position K2 from the acetabular end point. Thus, in the example shown in FIG. 29, the positions at which the space widths become the minimum differ in the past and the present. Further, in the position K1 at which the present space width becomes the minimum, the space width is H2 on the past image, and the space width is larger in the past than in the present. Further, in the position K2 in which the space width is the minimum in the past, the space width is G3 in the present and is larger than that of the past.

Next, in step S53 of FIG. 27, the corresponding points on the images of the past and the present displayed on the display screen of the display unit 32 are displayed on the corresponding other images.

Figure 30A:
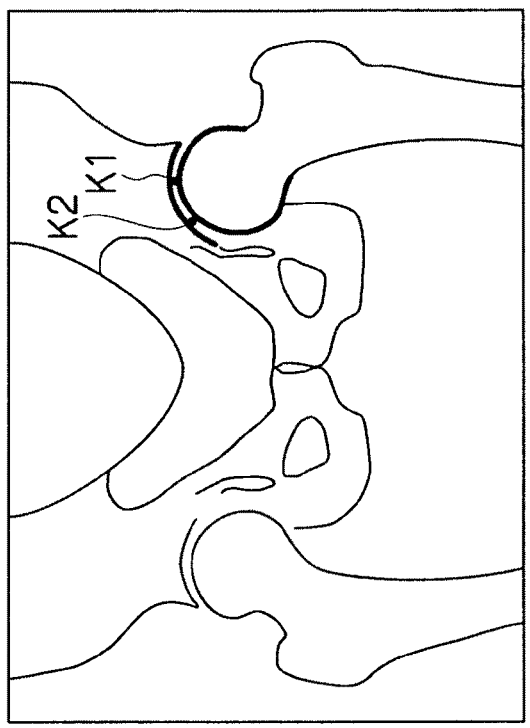
FIGS. 30A and 30B are explanatory views showing a display example of images in the first display method.
Figure 30B:
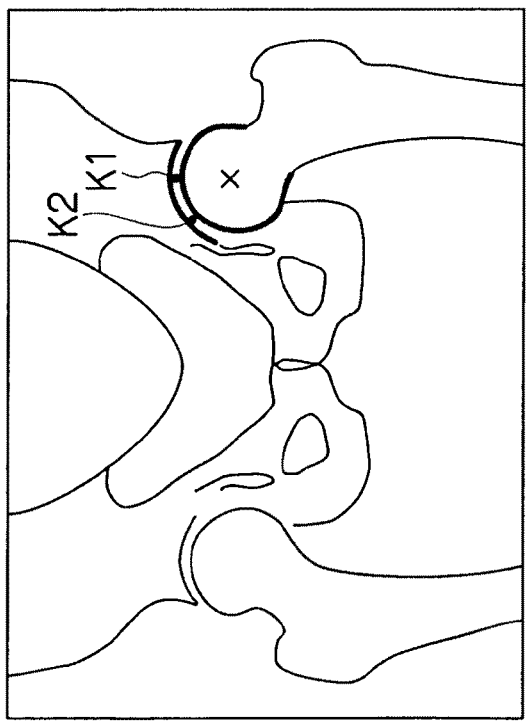

More specifically, which positions the position K1 at which the space width becomes the minimum in the space width graph g of the present and the position K2 at which the space width becomes the minimum in the space width graph h of the past shown in FIG. 29 correspond to on the images of the past and the present which are laterally displayed on the display screen as shown in FIGS. 30A and 30B are displayed.

By display like this, to which position the position at which the previous minimum space width is measured corresponds this time, and conversely, where the position at which the minimum space width is measured this time was at the previous time can be easily confirmed, and this is very useful for comparison in diagnosis in the observation over time.

Next, a second display method for displaying the joint space width measurement results by bringing the results of the past and the present into correspondence with each other will be described.

FIG. 31 shows the process of the second display method for displaying the results of the past and the present by bringing them into correspondence with each other with respect to display of the joint space width measurement result by a flowchart.

The second display method displays which points on the image correspond to the points on the space width graph.

First, in step S60 of FIG. 31, the contour image is created from the hip joint images of the past and the present and the space width is measured. This is similar to step S50 in FIG. 27 in the aforementioned first display method.

Next, in step S61, the magnification ratios of the past image and the present image are matched with each other by using one or more of the pieces of information of the femoral head contour, the femoral head center, the acetabular contour, the approximation ellipse of the femoral head, the acetabular end point and the like. This step is also similar to step S51 of FIG. 27 in the aforementioned first display method, and as the information for use, use of two of the femoral head center and the femoral head contour is preferable, and thereby, the original images of the past and the present and the respective contour images are transformed to have the same magnification ratio.

Next, in step S62, positioning of the acetabular end points is performed, and the start point and the end point of the space width graph are matched with each other, and this is also similar to step S52 of FIG. 27.

Figure 32:
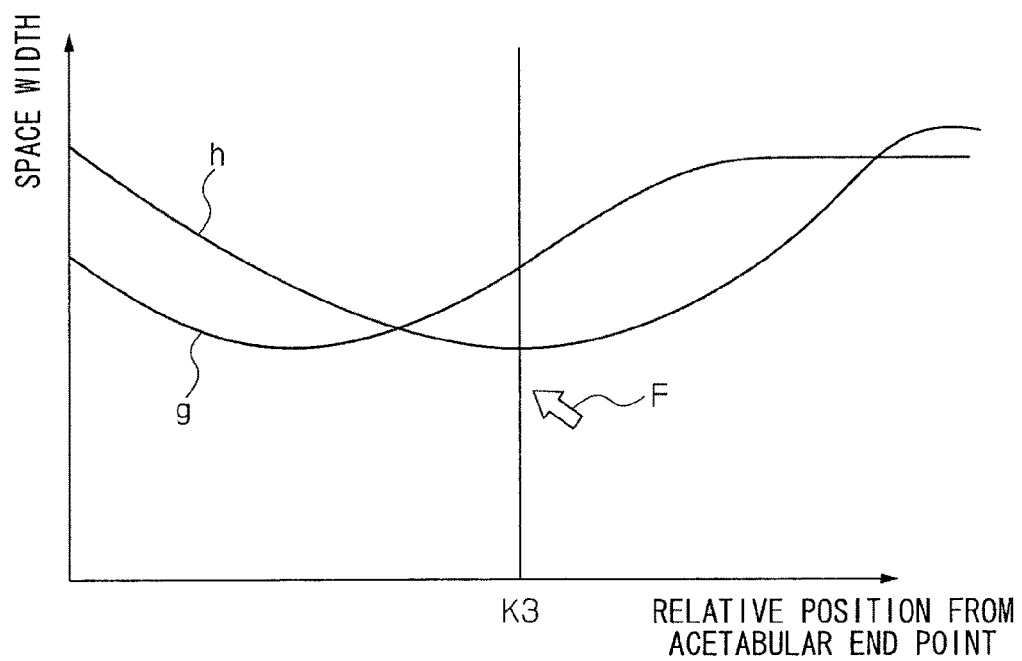
FIG. 32 is a chart showing an example of a space width graph in the second display method.

Next in step S63, the space width is graphically displayed with the acetabular contour as the axis of abscissas. FIG. 32 shows an example of the space width graph of this case.

In FIG. 32, "g" represents the space width graph in the present image, "h" represents the space width graph in the past image, the axis of abscissas represents the relative position from the acetabular end point along the acetabular contour in each of the present and past images, and the axis of ordinates represent the value of the space width.

Next, in step S64, correspondence relationship of the point on the space width graph and the point on the image with the acetabular contour position as a basis is displayed.

More specifically, as shown by the arrow "F" in FIG. 32 in the space width graph screen displayed on the display screen of the display unit 32 in FIG. 32, when a certain point is clicked via the information input unit 28, the vertical straight line is generated on the axis of abscissas at a position "K3" in the data processing unit 30, and is displayed on the display screen. Meanwhile, by processing in the data processing unit 30, in the past image and the present image which are displayed by being laterally arranged on the display screen, the corresponding position K3 of the space is displayed.

As above, in the present display method, when a certain point is clicked in the space width graph, the points on the images corresponding to the certain point are displayed.

Next, a third display method for displaying the joint space width measurement results by bringing the results of the past and the present into correspondence with each other will be described.

In the third display method, when a certain point on the image is clicked, the point corresponding to it on the space width graph is displayed, contrary to the aforementioned second display method. At this time, if the point on the present image, for example, is clicked, the point on the space width graph corresponding to this is displayed, and the point on the past image corresponding to this is displayed.

Figure 34:
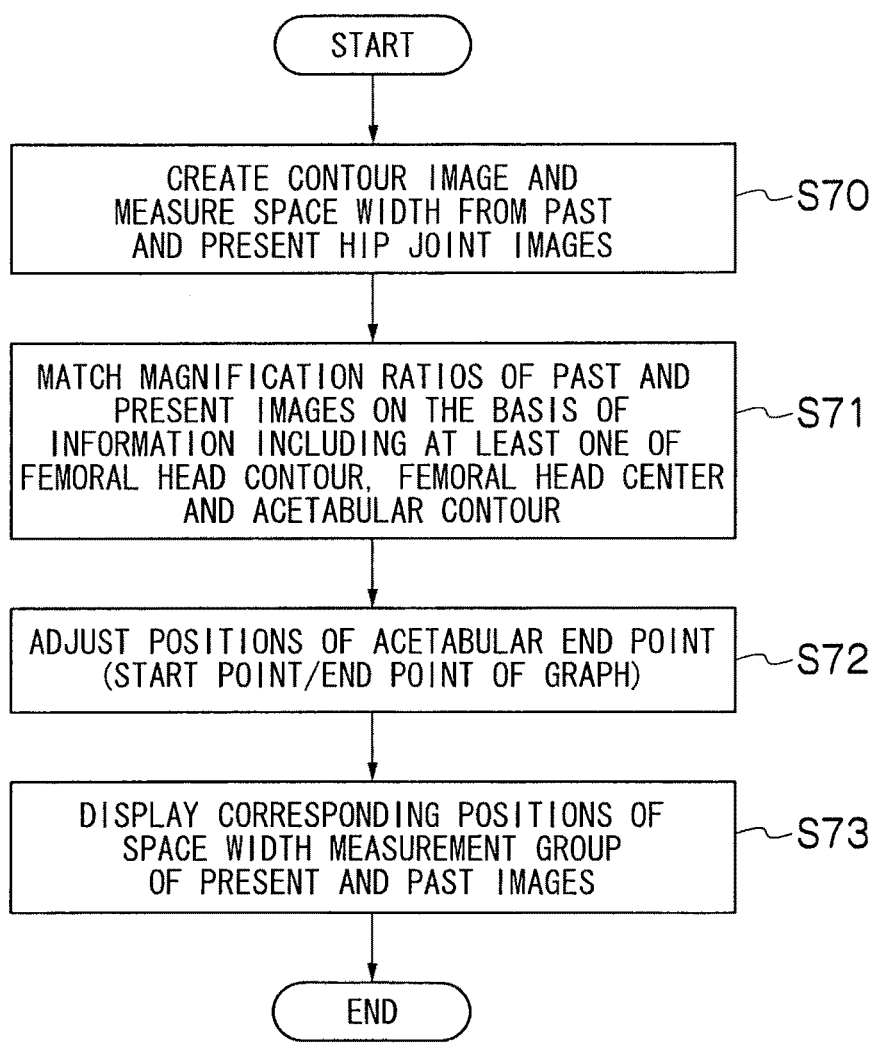
FIG. 34 is a flowchart showing a process of a third display method concerning display of a measurement result of a space width of a joint.

FIG. 34 shows the process of the third display method about display of the joint space width measurement result by a flowchart.

As shown in FIG. 34, steps S70 to S72 are the same as steps S50 to S52 of the flowchart of FIG. 27 in the aforementioned first display method.

In step S73 of FIG. 34, the corresponding positions of the space width measurement group of the present and the past images are displayed. More specifically, in FIGS. 33A and 33B, for example, if the position K3 of a certain space width is clicked on the display screen in the past image at the left side, the position K3 of the space width corresponding to the position of that space width is displayed on the present image at the right side, and further in the space width graph shown in FIG. 32, the vertical line is displayed at the relative position K3 from the acetabular end point in the corresponding acetabular contour.

Thereby, with respect to the position K3 of the space on the image, the position K3 on the space width graph corresponding to this is found, and the value of the space width is found.

Figure 33A:
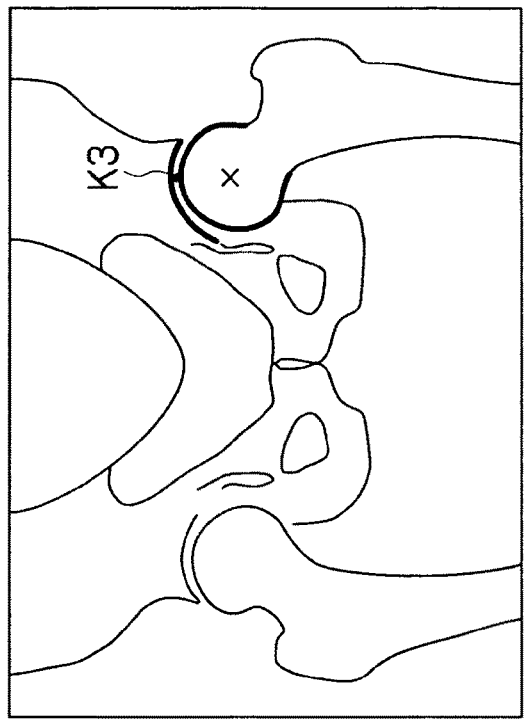
FIGS. 33A and 33B are explanatory views showing a display example of an image in the second display method.
Figure 33B:
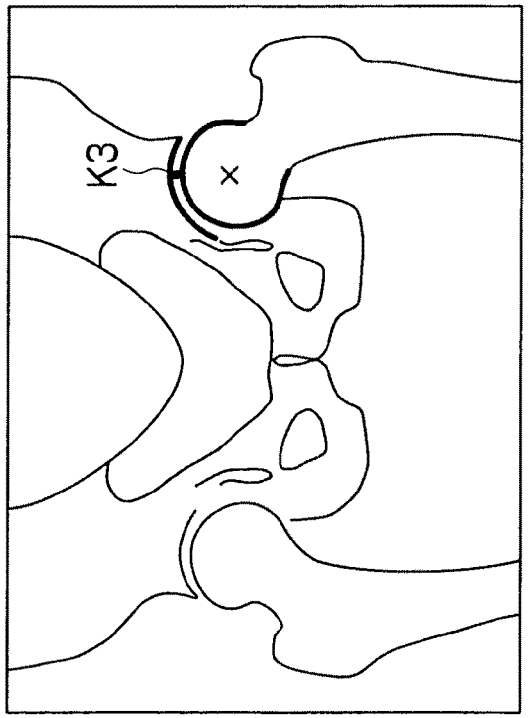

In the example mentioned now, a certain space position K3 is designated on the past image at the left side of FIGS. 33A and 33B at first, but a certain space position may be designated on the present image at the right side as a matter of fact.

In this case, the space position on the past image corresponding to this and the corresponding space position on the space width graph of FIG. 32 are displayed.

Next, a fourth display method for displaying the joint space width measurement results by bringing the past and the present results into correspondence with each other will be described.

In each of the embodiments described thus far, at the time of obtaining the joint space, the joint space is obtained by the relative position from the acetabular end points along the acetabular contour, but in the fourth display method, the joint space is measured by the angle from the reference line drawn from the femoral head center.

Figure 35:
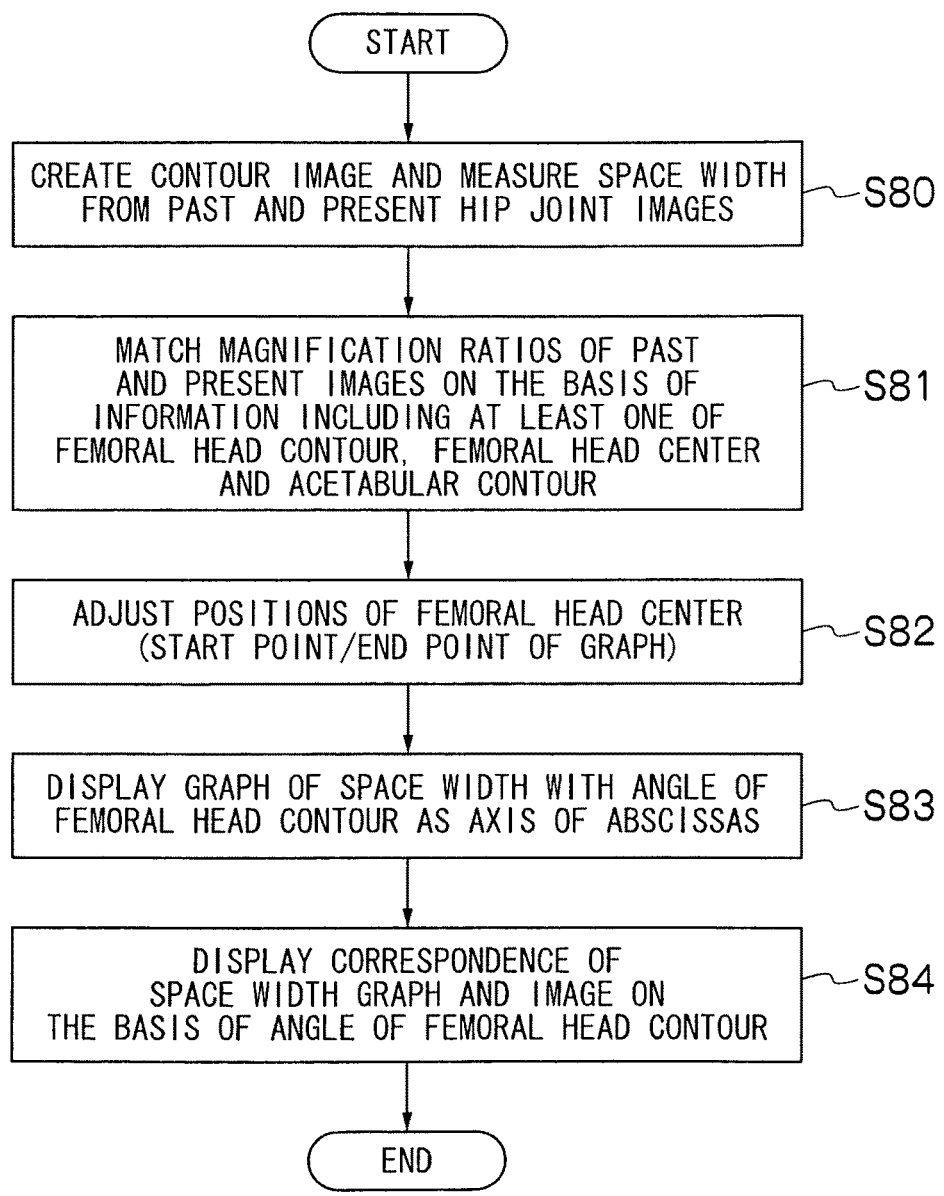
FIG. 35 is a flowchart showing a process of a fourth display method concerning display of a measurement result of a space width of a joint.

FIG. 35 shows the process of the fourth display method about the display of the joint space width measurement result by a flowchart.

Steps S80 and S81 of FIG. 35 are similar to steps S50 and S51 in FIG. 27 of the aforementioned first display method.

Next, in step S82, the femoral head centers are positioned, and the start point and the end point of the space width graph are determined. More specifically, with a certain half line extending from the femoral head center as the reference line, the space width at the portion where the half line intersects the femoral head contour and the acetabular contour is set as the start point of the space width graph. Meanwhile, the end point does not necessarily have to be determined, and the end points may differ in the past image and the preset image.

Next, in step S83, the space width graph with the angle of the femoral head contour as the axis of abscissas is created, and is displayed on the display screen of the display unit 32. FIG. 36 shows the space width graph of this case. In FIG. 36, g represents the space width graph in the present image, h represents the space width graph in the past image, and the axis of ordinates represents the value of the space width. Further, in the fourth display method, the axis of abscissas represents the angles from the reference lines α and α' extending from the femoral head centers C and C' in the present and past images, respectively.

Figure 37B:
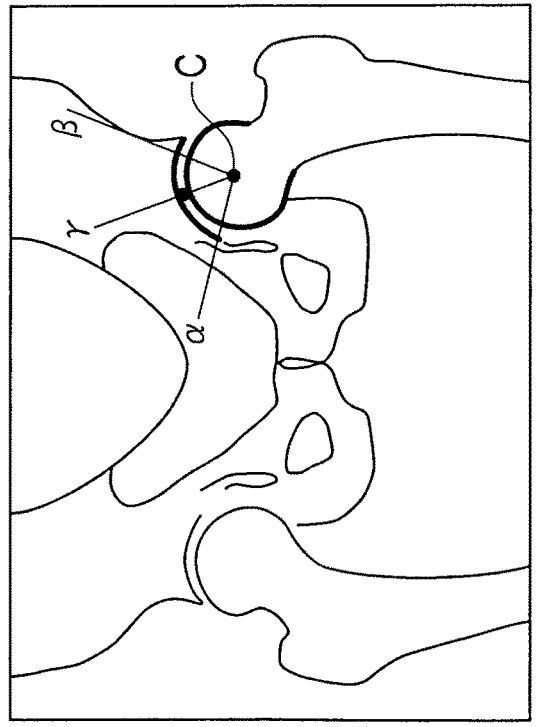
FIGS. 37A and 37B are an explanatory view showing a display example of an image in the fourth display method.
Figure 37A:
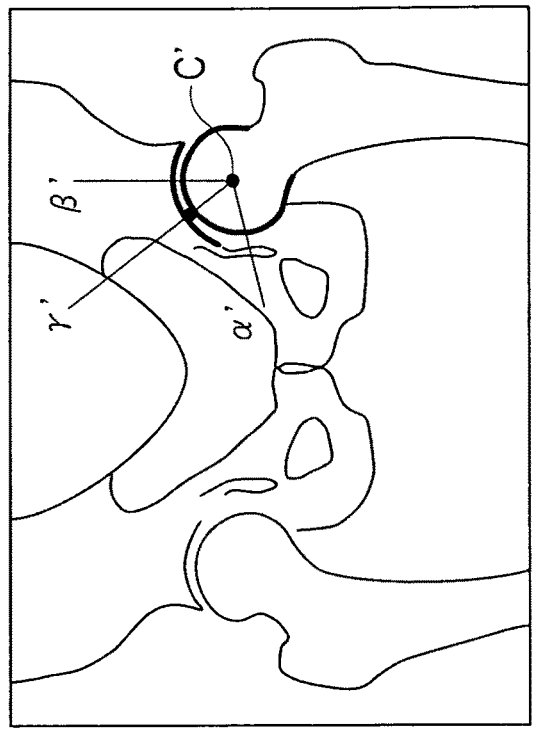

Next, in step S84, correspondence of the point on the space width graph and the point on the image with the angle of the femoral head contour as the basis is displayed. More specifically, when the position of an angle γ (γ') from the reference line α(α') from the femoral head center is clicked in the space width graph of FIG. 36, the position on the image corresponding to this is displayed on the past and the present images at the left and right as shown in FIGS. 37A and 37B.

Like this, in order to designate the position of the space width, not only the distance from the acetabular end point along the acetabular contour but also the angle around the femoral head center can be used.

Next, a fifth display method for displaying the joint space width measurement results by bringing the measurement results of the past and the present into correspondence with each other will be described.

In the present fifth display method, if a certain point on the image is clicked, the point on the space width graph corresponding to it is displayed, contrary to the aforementioned fourth display method. At this time, if the point on the present image is clicked, for example, the point on the space width graph corresponding to this is displayed, and the point on the past image corresponding to this is displayed.

Figure 38:
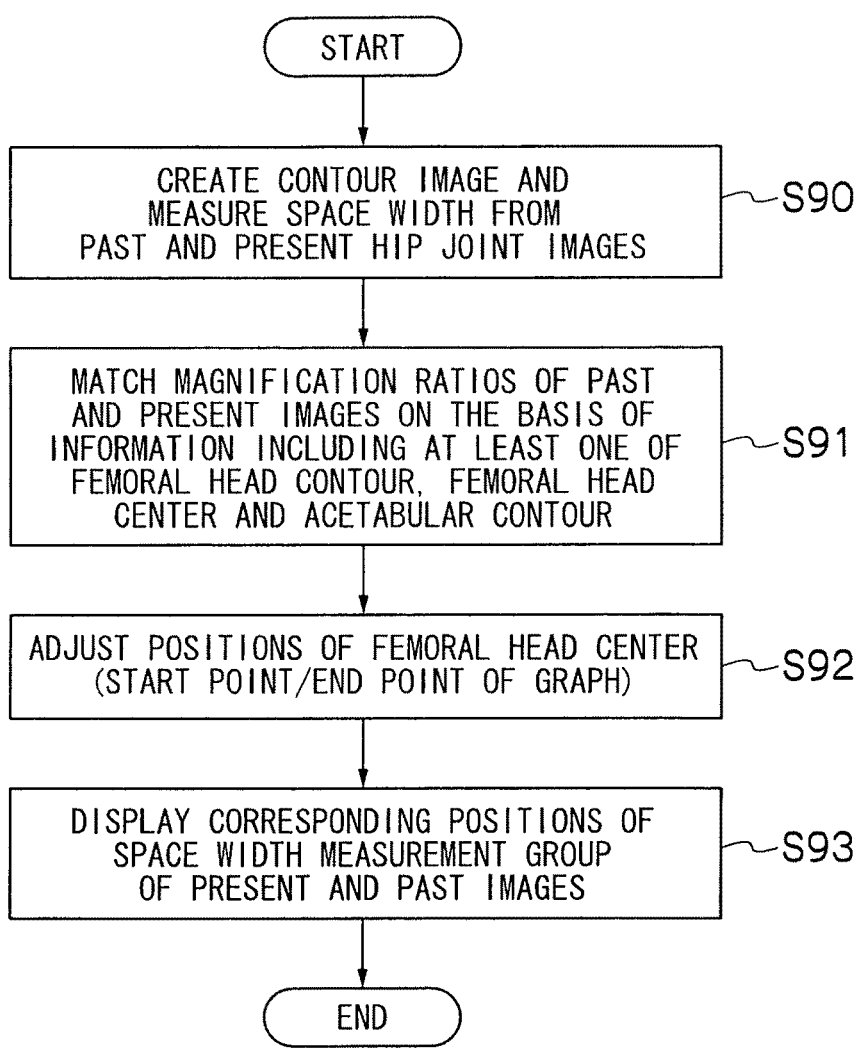
FIG. 38 is a flowchart showing a process of a fifth display method concerning display of a measurement result of a space width of a joint.

FIG. 38 shows the process of the fifth display method about display of the joint space width measurement result by a flowchart.

Steps S90 to S92 of FIG. 38 are similar to steps S80 to S82 of FIG. 35 of the aforementioned fourth display method.

Next, in step S93 of FIG. 38, the corresponding positions of the space width measurement group of the present and past images are displayed. More specifically, in FIGS. 37A and 37B, if the position of the space width in which the angle from the reference line α from the head center C is γ is clicked on the display screen in the past image at the left side, for example, the position γ' of the space width corresponding to the position of the space width is displayed in the present image at the right side, and the vertical line representing the position at the corresponding angle γ from the reference line α of the femoral head center is displayed in the space width graph shown in FIG. 36.

Thereby, with respect to the position γ of the space on the image, the position γ on the space width graph corresponding to this is found, and the value of the space width is found.

In the example mentioned now, a certain space position γ is designated on the past image at the left side of FIGS. 37A and 37B at first, but a certain space position γ' may be designated on the present image at the right side as a matter of course. In this case, the space position on the past image corresponding to this, and the corresponding space position on the space width graph of FIG. 36 are displayed.

Next, a sixth display method for displaying the joint space width measurement results by bringing the measurement results of the past and the present into correspondence with each other will be described.

Figure 39:
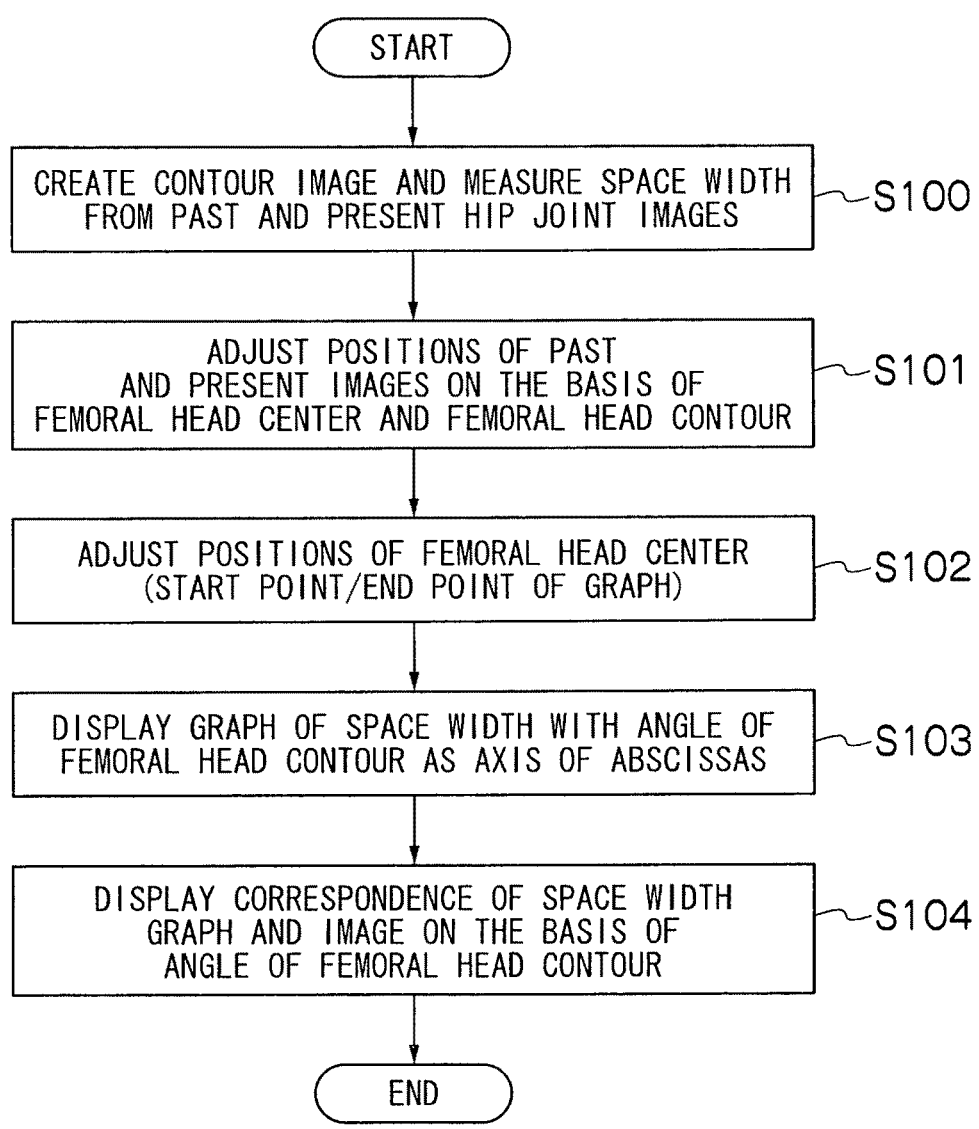
FIG. 39 is a flowchart showing a process of a sixth display method concerning display of a measurement result of a space width of a joint.

FIG. 39 shows the process of the sixth display method about display of the joint space width measurement result by a flowchart.

As is known from the flowchart of FIG. 39, in the present embodiment, only step S101 differs from step S81 in FIG. 35, and the other steps are similar to those of the aforementioned fourth display method.

More specifically, in the present display method, in step S100, a contour image is created from the past and present hip joint images, and the space width is measured. Thereafter, in step S101, at the time of positioning of the past and the present images, only the femoral head centers and the femoral head contours are used. Further, in step S101, at the time of positioning of the past and the present images, rotation is also obtained.

In the example of the image shown in FIGS. 37A and 37B, the corresponding positions α and α', and β and β' differ significantly in the past image and the present image, but these corresponding positions usually become substantially the same positions.

In each of the display methods described in detail above, the positions of the space width of the present and the past which are required for space width measurement are brought into correspondence with each other. Therefore, the corresponding places at the present and in the past can be quantitatively compared, and therefore, difference depending on a user does not exist. Further, quantitative evaluation with respect to temporal change of the space width is enabled.

For positioning of the acetabular end points, only one of them may be positioned. If there are any points which can be positioned other than the start point and the end point of the space width graph, they may be used. The axis of abscissas in the space width graph can be matched in the actual size. For example, in the case of the relative position from the acetabular end point along the acetabular contour, the axis of abscissas can be matched in [mm].

In the examples described above, the past image and the present image are compared, but the past images may be compared. Further, when only the present image is available, and the past image is not available, the space widths at the left and right of a hip joint may be compared.

Further, the sequence of positioning and measurement of the space width may be changed, or may be processed in parallel by using a dual core.

Further, the joint space width measuring process of the present embodiment is implemented by a program stored in the memory attached to the control unit which controls the entire system which is not illustrated, for example. More specifically, the program which executes the joint space width measurement process is read from the memory by the control unit, and in accordance with the program, the contours of a pair of bones constituting a joint are detected from the inputted joint image. Based on the aforementioned detected contours, the measurement range of the space width of the aforementioned joint is set, and in the aforementioned set measurement range, the space width which is the distance of the aforementioned pair of bones is calculated. Based on the aforementioned detected contours, the contour image is formed, and based on the aforementioned calculated space width, the space width graph in which the position in the aforementioned joint and the aforementioned space width are brought into correspondence with each other is formed. The aforementioned joint image or the aforementioned contour image, and the aforementioned space width graph are stored. On the display screen for displaying the aforementioned inputted joint image or the aforementioned stored joint image, or the contour image formed from these joint images, and the aforementioned space width graph corresponding to these joint images, processing of displaying a predetermined point on the aforementioned joint image or the aforementioned contour image corresponding to a predetermined point on the aforementioned space width graph is implemented.

The present program is not limited to the one stored in the memory which is attached to the control unit as above, but the program may be recorded in a memory medium (removable medium) configured to be attachable to and detachable from the present feature point detecting device such as, for example, a PC card and a CD-ROM, and may be read to the present device through the interface corresponding to the removable medium.

The system for measuring space width of joint, the method for measuring space width of joint and the program of the presently disclosed subject matter are described in detail above, but the presently disclosed subject matter is not limited to the above examples, and it goes without saying that various improvements and modifications may be performed in the range without departing from the gist of the presently disclosed subject matter.

What is claimed is:

1. A system for measuring space width of joint, comprising:
   a joint image input unit which inputs an image of a joint;
   a contour detection unit which detects contours of a pair of bones constituting the joint;
   a measurement range setting unit which sets a measurement range of a space of the joint based on the contours detected by the contour detection unit;
   a space width calculation unit which calculates a plurality of space widths each of which is indicated by a distance value between the pair of bones in the measurement range set by the measurement range setting unit as a distance value between two points at which a plurality of predetermined straight lines arranged in a predetermined rule each intersects with the contours of the pair of bones in the measurement range as a space width at each position; and
   a display unit which displays at least one of an average value, a median value, a minimum value, and a graph display of space widths based on the plurality of space widths calculated by the space width calculation unit.

2. The system for measuring the space width of the joint according to claim 1, further comprising an information input unit which inputs information to the system,
   wherein the contour detection unit detects the contours by interpolating a plurality of points on the contour which are inputted by the information input unit.

3. The system for measuring the space width of the joint according to claim 1,
   wherein the contour detection unit detects the contours based on a plurality of edge points in an edge image formed by performing edge detection for the image of the joint inputted by the joint image input unit.

4. The system for measuring the space width of the joint according to claim 3, further comprising an information input unit which inputs information to the system,
   wherein the plurality of edge points are inputted by the information input unit.

5. The system for measuring the space width of the joint according to claim 1,
   wherein the measurement range setting unit sets a whole of the contours detected by the contour detection unit as the measurement range.

6. The system for measuring the space width of the joint according to claim 1,
   wherein the predetermined straight line extends radially from a predetermined point.

7. The system for measuring the space width of the joint according to claim 6,
   wherein the predetermined point is a femoral head center point.

8. The system for measuring the space width of the joint according to claim 1,
   wherein the predetermined straight line is perpendicular to one fixed straight line different from the predetermined straight line.

9. The system for measuring the space width of the joint according to claim 8,
   wherein the fixed straight line is a straight line connecting lower ends of a left and a right teardrop-shaped representation of the contours detect by the contour detection unit.

10. The system for measuring the space width of the joint according to claim 1,
    wherein the space width calculation unit calculates a neighborhood average space width which is an average value of an arbitrary space width of the serial data of a plurality of space widths and one or more neighborhood space widths which are present in a vicinity of the arbitrary space width.

11. The system for measuring the space width of the joint according to claim 1,
    wherein the space width calculation unit calculates a median value of an arbitrary space width of serial data of a plurality of space widths and two or more neighborhood space widths which are present in a vicinity of the arbitrary space width.

12. The system for measuring the space width of the joint according to claim 1,
    wherein: the space width is a minimum value of serial data of a plurality of space widths, and
    the display unit displays a portion corresponding to the space width at which the minimum value is calculated by emphasizing the portion.

13. The system for measuring the space width of the joint according to claim 1,
wherein the display unit displays a graph of serial data of a plurality of space widths.

14. The system for measuring the space width of the joint according to claim 13,
wherein the display unit causes the displayed graph to vary in accordance with a value of the space width.

15. The system for measuring the space width of the joint according to claim 13,
wherein: the display unit displays the image of the joint inputted by the joint image input unit, and
when an arbitrary point on the displayed graph is designated, a corresponding portion of the contour in the image of the joint is displayed by being emphasized.

16. The system for measuring the space width of the joint according to claim 1,
wherein the display unit switches a kind of display of the value of the space width in accordance with the value of the space width.

17. The system for measuring the space width of the joint according to claim 1,
wherein the display unit displays the image of a joint which is inputted from the joint image input unit, and switches a kind of display of the portions corresponding to the contour and the space width in the image of the joint in accordance with a value of the space width.

18. The system for measuring the space width of the joint according to claim 1, further comprising a storage unit which stores at least any one of the image of the joint inputted by the joint image input unit, the space width calculated by the space width calculation unit, and measurement-related information including the contour and the measurement range used for calculating the space width.

19. The system for measuring the space width of the joint according to claim 18,
wherein the display unit includes an image position adjustment unit which adjusts a position of a present image which is the image of the joint inputted at present by the joint image input unit and a position of a past image which is the image of the joint of the past stored in the storage unit, or adjusts positions of a plurality of the past images to display the images.

20. The system for measuring the space width of the joint according to claim 19,
wherein the display unit includes a display specification adjustment unit which displays the present image and the past image, or the plurality of the past images by superimposing the images on one another, displays the images by switching the images, or displays the images by arranging the images side by side.

21. The system for measuring the space width of the joint according to claim 19,
wherein the storage unit stores image positioning information including information of positions of the images, orientations of the images and sizes of the images in the display unit when the image position adjustment unit adjusts the positions of the present image and the past image, or the positions of the plurality of the past images.

22. The system for measuring the space width of the joint according to claim 21,
wherein the image position adjustment unit adjusts the positions of the present image and the past image, or the positions of the plurality of the past images based on the image positioning information stored in the storage unit to display the images.

23. The system for measuring the space width of the joint according to claim 18,
wherein the display unit includes an information position adjustment unit which adjusts positions of the measurement-related information of the present and the measurement-related information of the past, or adjusts positions of a plurality of pieces of the measurement-related information of the past to display the information.

24. The system for measuring the space width of the joint according to claim 1,
wherein the joint is a hip joint.

25. The system for measuring the space width of the joint according to claim 1, further comprising:
a contour image forming unit which forms a contour image based on contours detected by the contour detection unit;
a space width graph creating unit which forms a space width graph in which a position in the joint and a space width are brought into correspondence with each other based on the space width calculated by the space width calculation unit; and
a storage unit which stores the image of the joint or the contour image, and the space width graph,
wherein: the display unit displays the image of the joint inputted from the image input unit, or the image of the joint stored in the storage unit, or the contour images obtained from these joint images, and the space width graph corresponding to the joint images, and
the display unit displays a predetermined point on the image of the joint or the contour image, the predetermined point corresponding to a predetermined point on the space width graph.

26. The system for measuring the space width of the joint according to claim 25,
wherein the predetermined point on the space width graph is a point indicating a minimum space width.

27. The system for measuring the space width of the joint according to claim 25, further comprising an information input unit for inputting a designation instruction to designate a predetermined point on the image of the joint, the contour image or the space width graph displayed on the display unit,
wherein a plurality of images of the joint which are inputted at different time points, or a plurality of contour images obtained from the images of the joint are displayed by being arranged side by side on the display unit, a plurality of the space width graphs corresponding to the images of the joint are superimposed on one another, and are displayed on a place different from a place of the display unit on which the image of the joint or the contour image is displayed, and
when an arbitrary point on the space width graph is designated as a point on the image of the joint or the contour image, the point corresponding to the arbitrary point is displayed.

28. The system for measuring the space width of the joint according to claim 25, further comprising an information input unit for inputting a designation instruction to designate a predetermined point on the image of the joint, the contour image or the space width graph which is displayed on the display unit,
wherein a plurality of images of the joint which are inputted at different time points, or a plurality of contour images obtained from the images of the joint are displayed by being arranged side by side on the display unit, a plurality of the space width graphs corresponding to the images of the joint are superimposed on one another, and are displayed on a place different from a place of the display unit on which the image of the joint or the contour image is displayed, and when a predetermined point on a joint space is designated on the image of the joint or the contour image as a point on the space width graph, the point corresponding to the predetermined point is displayed.

29. The system for measuring the space width of the joint according to claim 25, wherein the space width graph represents an axis of abscissas as a relative position from an acetabular end point of the joint under measurement, and an axis of ordinates as a space width in the relative position of the joint.

30. The system for measuring the space width of the joint according to claim 25, wherein the space width graph represents an axis of abscissas as an angle of a half line with a center of a femoral head of the joint under measurement as a start point from a predetermined reference line, and an axis of ordinates as a space width in a position where the half line intersects the space of the joint.

31. A method for measuring space width of joint, comprising:

a joint image input step of inputting an image of a joint;

a contour detecting step of detecting contours of a pair of bones constituting the joint;

a measurement range setting step of setting a measurement range of a space of the joint based on the contours detected in the contour detecting step;

a space width calculating step of calculating a plurality of space widths each of which is a distance between the pair of bones within the measurement range set in the measurement range setting step as a distance value between two points at which a plurality of predetermined straight lines arranged in a predetermined rule each intersects with the contours of the pair of bones in the measurement range as a space width at each position; and a display step of displaying at least one of an average value, a median value, a minimum value, and a graph display of space widths based on the plurality of space widths calculated in the space width calculating step.

32. A recording medium comprising a computer program causing a computer to execute a process for measuring a joint space width, the process comprising:

a joint image input step of inputting an image of a joint;

a contour detecting step of detecting contours of a pair of bones constituting the joint;

a measurement range setting step of setting a measurement range of a space of the joint based on the contours detected in the contour detecting step;

a space width calculating step of calculating a plurality of space widths each of which is a distance between the pair of bones within the measurement range set by the measurement range setting step as a distance value between two points at which a plurality of predetermined straight lines arranged in a predetermined rule each intersects with the contours of the pair of bones in the measurement range as a space width at each position; and a display step of displaying at least one of an average value, a median value, a minimum value, and a graph display of space widths based on the plurality of space widths calculated in the space width calculating step.

* * * * *